(12) United States Patent
Hell et al.

(10) Patent No.: US 8,580,579 B2
(45) Date of Patent: Nov. 12, 2013

(54) HYDROPHILIC AND LIPOPHILIC RHODAMINES FOR LABELLING AND IMAGING

(75) Inventors: Stefan Hell, Goettingen (DE); Vladimir N. Belov, Goettingen (DE); Kirill Kolmakov, St. Petersburg (RU); Volker Westphal, Hannover (DE); Marcel Lauterbach, Goettingen (DE); Stefan Jakobs, Goettingen (DE); Christian Wurm, Goettingen (DE); Christian Eggeling, Goettingen (DE); Christian Ringemann, Goettingen (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 67 days.

(21) Appl. No.: 13/266,775

(22) PCT Filed: Apr. 26, 2010

(86) PCT No.: PCT/EP2010/002558
§ 371 (c)(1),
(2), (4) Date: Jan. 13, 2012

(87) PCT Pub. No.: WO2010/124833
PCT Pub. Date: Nov. 4, 2010

(65) Prior Publication Data
US 2012/0100559 A1   Apr. 26, 2012

(30) Foreign Application Priority Data
Apr. 28, 2009  (EP) ..................... 09005886

(51) Int. Cl.
G01N 33/533 (2006.01)
G01N 33/532 (2006.01)
G01N 21/76 (2006.01)

(52) U.S. Cl.
USPC ............................ 436/546; 436/544; 436/172

(58) Field of Classification Search
None
See application file for complete search history.

(56) References Cited

U.S. PATENT DOCUMENTS 6,372,907 B1 * 4/2002 Lee et al. ................. 546/41

FOREIGN PATENT DOCUMENTS

JP         2002168867 A  *  6/2002

* cited by examiner

Primary Examiner — Shafiqul Haq
(74) Attorney, Agent, or Firm — Caesar, Rivise, Bernstein, Cohen & Pokotilow, Ltd.

(57) ABSTRACT

The invention relates to novel and improved photostable rhodamine dyes of the general structural formulae I or II and their uses as fluorescent markers, e.g. for immunostainings and spectroscopic and microscopic applications, in particular in conventional and stimulated emission depletion (STED) microscopy and fluorescence correlation spectroscopy. The partially deuterated analogues are useful as molecular mass distribution tags in mass spectroscopic applications, wherein $R^1$=an unsubstituted or substituted alkyl group, including a cycloalkyl group, or heterocycloalkyl group; $R^2$=H, an unsubstituted or substituted alkyl group, including a cycloalkyl group, or heterocycloalkyl group, or an unsubstituted or substituted aryl group or heteroaryl group, or any combination of such groups; $X=CH_2$, $C=O$, $C=NOR^a$, $C=NNR^aNR^b$, $CH(OR^a)$, $O$, $S$, $SO$, $SO_2$, or any other derivatives of these groups, with Ra and Rb independently being H or an organic residue, in particular an unsubstituted or substituted (cyclo)alkyl group or heterocycloalkyl group, an unsubstituted or substituted aryl group or heteroaryl group; Z=a negatively charged group with 1, 2, 3, 4 or 5 charges per anion.

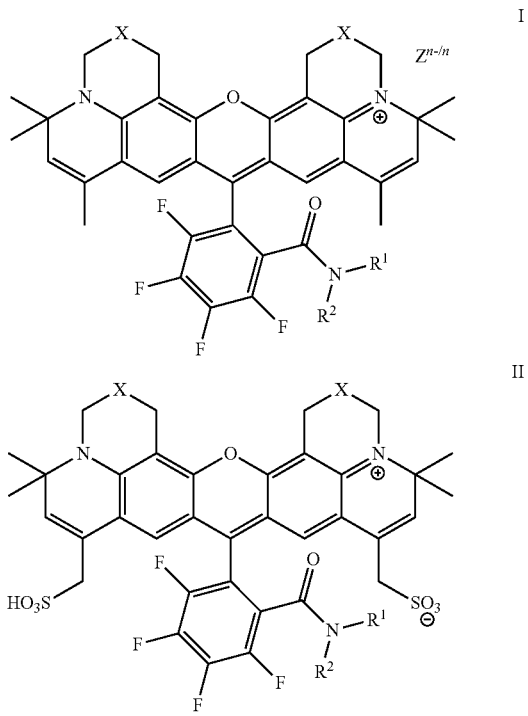

13 Claims, 5 Drawing Sheets

HYDROPHILIC AND LIPOPHILIC RHODAMINES FOR LABELLING AND IMAGING

BACKGROUND OF THE INVENTION

Rhodamine dyes are known to be photostable fluorescent labels with large absorption coefficients, high fluorescent quantum yields, and low degree of triplet formation. Rhodamines are widely used both as laser dyes and fluorescent compounds for labelling proteins, nucleic acids, lipids, carbohydrates, toxins, hormones and other biomolecules (e.g. R. P. Haugland, *A Guide to Fluorescent Probes and Labelling Technologies*, Invitrogen, Carlsbad, 2005, pp. 11-37).

Rhodamines have also served for practical implementations of some new physical concepts that overcome the diffraction limit by switching between the dark and bright states of a fluorescent marker (e.g. S. W. Hell, *Science* 2007, 317, 1749-1753). For example, a very important novel method of the stimulated emission depletion (STED) microscopy uses the ground (singlet) state of the fluorophore ($S_0$) as a dark state, and the first excited state ($S_1$) as a bright one. In practical applications of the STED method, a focused pulse excites fluorescence in a small spot (with dimensions limited by diffraction), and immediately after that a red-shifted doughnut-shaped STED beam switches off the fluorescence of excited molecules by stimulated emission ($S_1 \rightarrow S_0$) everywhere, except in the very center of the doughnut, where the quenching intensity is zero. For squeezing the fluorescence to a very small central spot, the depletion rate should exceed the rate of the spontaneous transition to a ground state $S_0$. Fluorescent lifetimes of organic fluorophores ($\tau_{fl} \sim 10^{-9}$ s) and their optical cross-sections of the $S_1 \rightarrow S_0$ transitions ($\sigma \sim 10^{-16}$ cm$^2$) imply that the STED-pulse should have a very high power $I_{STED} \gg I_S \equiv (\sigma \tau_{fl})^{-1} \sim 10^{25}$ photons/(cm$^2$×s)≅10 MW/cm$^2$. $I_S$ is a threshold intensity depending on the dye employed and the depletion wavelength used. The resolution enhancement scales roughly with $\sqrt{1+I_{STED}/I_S}$. These huge light intensities inevitably cause photobleaching of fluorophores, and therefore STED microscopy ultimately requires the most photostable fluorescent dyes.

Along with the relatively long lifetimes of the excited states (>3 ns), other important qualities of the STED and common fluorescent dyes are high fluorescent quantum yields ($\Phi_{fl}$) and oscillator strengths (high absorption coefficients), low rate of the triplet state formation, sufficient solubility in water or aqueous buffers and a reactive group (with a linker) for attaching a dye to a biological object or any other structure of interest. High $\Phi_{fl}$-values of the fluorescent labels conjugated with biomolecules are very important, as they improve the sensitivity of the imaging method. Moreover, if a resolution on the molecular scale is desired, or if only single molecules remain in the effective detection volume, the fluorophores should be suitable for the single molecule detection (e.g. in the method of fluorescence correlation spectroscopy—FCS). Recently, a far-field fluorescence "nanoscopy" based on switching the majority of the fluorescent molecules to a metastable dark state, such as the triplet, and calculating the position of those left or those that spontaneously returned to the ground state, has been introduced (S. W. Hell et. al, *Nature Meth.* 2008, 5, 943-945). This superresolution imaging method of the ground state depletion and single molecule return (GSDIM) requires new photostable fluorescent dyes with recovery times from several tens to several hundreds of milliseconds, minimal content of the dye in the ground state after the pump pulse and the possibility of the enhanced recovery caused by the irradiation with the UV laser (375 nm).

Water is the preferred solvent for operating with the reactive fluorescent dyes, because the conjugation reactions involving biologically relevant macromolecules (proteins, nucleic acids, carbohydrates) need to be performed in water or aqueous buffers. A marker is usually dissolved in an organic solvent, such as DMF or DMSO, and then added to the aqueous solution of the substrate. High concentrations of an organic solvent may cause protein denaturation, and hence should be avoided. On the other hand, a low coupling efficiency may be observed if the amount of the organic solvent is too low, and the marker precipitates in the reaction mixture. Water-soluble fluorescent markers are advantageous in this regard, because they do not require any organic solvents at all. Moreover, hydrophilic labels are less prone to aggregation and to non-specific binding with biological objects, especially membranes. Another advantageous feature of a potential fluorescent label is the availability of the two forms of the same dye (chromophore)—a lipophilic and hydrophilic one. The latter is indispensable for labelling of non-polar compounds (e.g. lipids in their non-polar domain), and the former is irreplaceable for labelling of polar substances (e.g. lipid head-groups).

Biological applications require fluorescent dyes absorbing in the red spectral region, because the excitation in this area reduces the background originating from autofluorescence of the cells (evident with UV and blue excitation). Very convenient is the excitation by the red He—Ne laser at 633 nm or with the 635 nm spectral line of a red diode laser, as well as with the 647 nm line of the krypton ion laser or with a diode laser emitting at 650 nm. Many fluorescent dyes have been prepared for these excitation sources. Various types of the commercially available dyes are given in Table 1. The lack of the "ideal" fluorescent dye for operating in the "red" spectral region becomes clear when one compares the performance of the available dyes under STED and FCS conditions in microscopy with very high light intensities and in the presence of air-oxygen.

TABLE 1

Commercially available organic fluorescent dyes for the excitation with He—Ne red laser (633 nm) or the 635 nm spectral line of red diode lasers.*

| Name | $\lambda_{max}$ (abs.) nm | $\lambda_{max}$ (fl.) nm | Solvent | $\epsilon \cdot 10^{-5}$ M$^{-1}$ cm$^{-1}$ | $\Phi_{fl}$ % | $\tau_{fl}$ ns | Provider (structure) | Solubility (polarity) |
|---|---|---|---|---|---|---|---|---|
| BODIPY® 630/650 | 625 | 640 | MeOH | 1.01 | "good" | 3.9 (H$_2$O) 4.4 (EtOH)[1] | Invitrogen (+) | DMSO, MeCN (non-polar) |
| Atto 633[2] | 629 | 657 | H$_2$O | 1.3 | 64 | 3.2 (H$_2$O) | Atto-tec (−) | DMF, DMSO, (H$_2$O) MeCN[2] |
| Alexa® 633[3] | 632 | 647 | MeOH | 1.0 | — | 3.2 | Invitrogen (+) | DMSO, H$_2$O[3] |

TABLE 1-continued

Commercially available organic fluorescent dyes for the excitation with He—Ne red laser (633 nm) or the 635 nm spectral line of red diode lasers.*

| Name | $\lambda_{max}$ (abs.) nm | $\lambda_{max}$ (fl.) nm | Solvent | $\epsilon \cdot 10^{-5}$ $M^{-1}$ $cm^{-1}$ | $\Phi_{fl}$ % | $\tau_{fl}$ ns | Provider (structure) | Solubility (polarity) |
|---|---|---|---|---|---|---|---|---|
| Atto 635 | 635 | 659 | $H_2O$ | 1.2 | 25 | 1.9 | Atto-tec (+) | DMF, DMSO, MeCN $(H_2O)^{2,4}$ |
| Atto 637[5] | 635 | 659 | $H_2O$ | 1.2 | 25 | 1.9 | Atto-tec (−) | $H_2O$, DMF, DMSO, MeCN[,4,5] |
| DyLight® 633 | 638 | 658 | unknown | 2.0 | — | — | Thermo Fisher Sci. (−) | — |
| DY-630[6] | 636 627[1] | 657 651[1] | EtOH $H_2O$ | 2.0 | Varies[6] | 0.21 $(H_2O)^{1,6}$ | Dyomics (+) | MeOH, EtOH, DMF, DMSO |
| DY-631[7], 632[7], 633[7], 634[7] | 635-637 | 657-658 | EtOH | 2.0 | — | — | Dyomics (+) | $H_2O$, MeOH, DMF, DMSO |
| DY-635 | 647 635[1] | 671 669[1] | EtOH $H_2O$ | 2.0 | — | 0.48 $(H_2O)^{1,6}$ | Dyomics (+) | MeOH, EtOH, DMF, DMSO |
| DY-636[8] | 645 | 671 | EtOH | 2.0 | — | — | Dyomics (+) | $H_2O$, EtOH, DMF, DMSO |
| DY-650[9] | 653 646[1] | 674 670 | EtOH $H_2O$ | 2.2 | — | 0.64 $(H_2O)^1$ | Dyomics (+) | MeOH, EtOH, DMF, DMSO |
| Evoblue 30[9] | 647 650[1] | 664 667[1] | EtOH $H_2O$ | 1.0 | — | 0.64 $(H_2O)^1$ | Fluka (+) | $H_2O$, MeOH, DMF, DMSO |
| Cy® 5[9] | 647 | 663 | $H_2O$ | 2.5 | 27 $(PBS)^{10}$ | 1 $(PBS)^{11}$ 0.9 $(H_2O)^1$ | GE Healthcare (+) | DMF, DMSO $(H_2O)$ |
| Alexa® 647[9,12,13] | 651 649[1] | 672 666[1] | MeOH $H_2O$ | 2.7 | 33[14] | 1.0 $(H_2O)^1$ | Invitrogen $(+)^{15}$ | $H_2O$, DMSO hydrophilic |
| Atto 647N[9,16,17] | 644 | 669 | $PBS^{11}$ | 1.5 | 65 | 3.4 | Atto-tec $(+)^{18}$ | DMF, DMSO (non-polar)[2] |
| DyLight® 649[9] | 646 | 674 | — | 2.5 | — | — | Thermo Fisher Sci. (−) | — |

*$\lambda_{max}$ (abs.), $\lambda_{max}$ (fl.): absorption and fluorescence maxima, respectively; $\epsilon$: molar extinction coefficient; $\tau_{fl}$: excited state lifetime.
[1] V. Buschmann, K. D. Weston, M. Sauer, *Bioconj. Chem.* 2003, 14, 195-204.
[2] According to the definition of the producer, this dye is "moderately hydrophilic".
[3] B. Agnew, K. R. Gee, T. G. Nyberg (Invitrogen), U.S. Pat. U.S. 2007/0249014.
[4] Slowly decomposes at pH > 8.5.
[5] Hydrophilic version of Atto 635.
[6] Addition of (bio)polymers (BSA, Tween20) increases the low fluorescence quantum yield of DY fluorophores (ca. 5% in $H_2O$) and their fluorescence lifetime: P. Czerney, F. Lehmann, M. Wenzel, V. Buschmann, A. Dietrich, G. J. Mohr, *Biol. Chem.* 2001, 382, 495-498.
[7] The same fluorophore as in DY-630; the solubility in water is increased due to the presence of up to 4 sulfonic acid residues.
[8] The same fluorophore as in DY-635; the solubility in water is increased due to the presence of two sulfonic acid residues.
[9] Fluorescence of this dye may be excited by the 647 nm line of the krypton ion laser or with diode laser emitting at 650 nm.
[10] R. B. Mujumdar, L. A. Ernst, S. R. Mujumdar, C. J. Lewis, A. S. Waggoner, *Bioconj. Chem.* 1993, 4, 105-111.
[11] www.iss.com/resources/fluorophores.html (PBS = phosphate buffer saline: 50 mM potassium phosphate, 150 mM NaCl, pH 7.2)
[12] Cy® 5 dye was shown to be "brighter" but less photostable than Alexa® 647: J. L. Ballard, V. K. Peeva, C. J. de Silva, J. L. Lynch, N. R. Swanson, *Mol. Biotechnol.* 2007, 36, 175-183.
[13] Photostability of the fluorescent dyes decreases in the following order: Alexa® 647 > Alexa® 633 > Cy® 5: R. P. Haugland, *A Guide to Fluorescent Probes and Labelling Technologies*, Invitrogen Corp., Carlsbad, 2005, p. 38.
[14] Measured at 22° C. relative to fluorescein in 0.01M NaOH ($\Phi_{fl}$ = 0.92); www.invitrogen.com/site/us/en/home/References/Molecular-Probes-The-Handbook/tables/Fluorescence-quantum-yields-and-lifetimes-for-Alexa-Fluor-dyes.html
[15] For the structure of Alexa 647, see Supporting Information of the following report: M. Bates, B. Huang, G. T. Dempsey, X. Zhuang, *Science*, 2007, 317, 1749-1753.
[16] According to the data of Atto-tec GmbH, photoresistance of the fluorescent dyes decreases in the following order: Atto 633 > Atto 647 > Cy® 5: www.atto-tec.de
[17] Mixture of two diastereomers with practically identical physical properties.
[18] For the structure of Atto 647N, see Supporting Information of the following report: C. Eggeling, C. Ringemann, R. Medda, G. Schwarzmann, K. Sandhoff, S. Polyakova, V. N. Belov, B. Hein, C. v. Middendorff, A. Schönle, S. W. Hell, *Nature*, 2009, 457, 1159-1163.

Analysis of the disclosed structures of the commercial fluorescent dyes matching the excitation with He—Ne red laser (633 nm) or 635 nm spectral line of red diode lasers (Tab. 1, FIG. 1) reveals that there is only one rhodamine among them: Alexa 633 was reported to be a "sulfonated rhodamine derivative" [J. E. Berlier et al., *J. Histochem. Cytochem.* 2003, 51, 1699-1712], and only in 2007 its structure has been reported [B. Agnew, K. R. Gee, T. G. Nyberg (Invitrogen), US Pat. 2007/0249014]. Along with rhodamines, the following substance classes were considered as leads for developing of the new fluorescent dyes: BODIPY® derivatives (represented by BODYPY® 630/650 in FIG. 4), carbopyronines (Atto 635 and 647), cyanine dyes (Cy® 5 and Alexa 647), structurally related hybrids of cyanine dyes and benzopyranes (DY-630/635/650) and oxazines (Evoblue 30). BODIPY® derivatives have a substantial drawback: sometimes, fluorescence intensity of their bioconjugates is not directly proportional to a number of labelled sites [R. P. Haugland, *A Guide to Fluorescent Probes and Labelling Technologies*, Invitrogen Corp., Carlsbad, 2005, p. 53]. Moreover, it is difficult to chemically modify a BODIPY residue in such a way that it becomes water-soluble and more photostable. Carbopyronines have been extensively studied by Drexhage et al. [e.g. A. Zilles, J. Arden-Jacob, K.-H. Drexhage, N. U. Kemnitzer, M. Hammers-Schneider (Atto-tec GmbH), WO 2005/003086 (13 Jan. 2005)]. The carbopyronine dye Atto 647N has been widely used for labelling in many "nanoscopic" studies. Quite recently first STED images of the living cells were recorded at a rate of 28 frames per seconds using this dye [V. Westphal, S. O. Rizzoli, M. A. Lauterbach, D. Kamin, R. Jahn, S. W. Hell, *Science* 2008, 320, 246-249]. In the course of this study, the movements of synaptic vesicles inside the axons of cultured neurons were recorded with a resolution of ca. 60 nm. Due to the low polarity of the dye, it sticks to the walls of micro capillary injection tubes, so that it proved difficult to properly inject its solutions into the cell. Sometimes bioconjugates of Atto 647N with antibodies display a strong increase in intensity of the second absorption peak at about 605 nm (irradiation at this wavelength does not generate any emission). Moreover, the lipophilic Atto 647N produced a considerable background in immunostaining experiments, largely due to its affinity to mitochondria. However, it is not easy to further improve the properties of the carbopyronine dye Atto 647N and make it more hydrophilic. Photostability of this dye was found to be better than that of the spectrally similar Alexa® 647. Therefore, the following order of the photoresistance can be derived: Atto 633>Atto 647N>Alexa® 647>Alexa® 633>Cy® 5 (see ref. to Table 1). Lower photostability and moderate $\Phi_{fl}$-values of cyanine dyes make them inappropriate as lead structures. Short lifetimes of the excited states and presumably low $\Phi_{fl}$-values of oxazines (e.g. Evoblue 30), as well as their moderate photostability, make the optimization of their properties not very promising.

Though rhodamines have been known and studied for a very long time, further improvements of their properties are still possible. For example, a very large bathochromic shift has been achieved for rhodamine 700 with a skeleton of the well-known rhodamine 101, in which the benzoic acid residue is replaced by trifluoromethyl group. All rhodamine derivatives with a perfluoroalkyl group at the position 9 were found to absorb and emit above 600 nm [M. Sauer et al., *J. Fluoresc.* 1995, 5, 247-261]. Unfortunately, they cannot be used as scaffolds for derivatization and further improvements, because the presence of the small and very strong electron acceptor group at C-9 of the xanthene fragment ("opposite" the oxygen atom) makes this position very vulnerable to the nucleophilic attack by water. Therefore, such rhodamines decolorize rapidly in aqueous solutions and loose their fluorescence. Up to now, the highest values for the adsorption and emission maxima (630 and 655 nm, respectively) for "normal" rhodamines have been achieved for the rigidized xanthene derivative 4 (Scheme 1) in 8 M urea solution [L. G. Lee, R. J. Graham, W. E. Werner, E. Swartzman, L. Lu, (Apptera Corp., USA), U.S. Pat. No. 6,372,907 (16 Apr. 2002)]. The drawback of compound 4 is its high lipophilicity (low polarity) and therefore low solubility in water or aqueous buffers. Another drawback of this compound is that it has a free carboxylic group which may give a colourless and non-fluorescent cyclic ester form. Though compound 4 is a valuable intermediate, it lacks any suitable reactive site for attaching to biomolecules. The carboxylic group in compound 4 is sterically hindered and low reactive. Moreover, the reaction of this carboxylic acid with primary amino groups (e.g. in proteins, lipids, etc.) would give amides which are known to form colourless and non-fluorescent cyclic spiroamides (due to addition of NH-group across the double tetra-substituted $C^9=C^{8a/8b}$ bond in the central xanthene ring).

Similar spectral values (624 and 644 nm for the absorption and emission, respectively) have been recorded in ethanol for the ethyl esters of the tetrachloro rhodamines AZ 84-AZ 95 [compounds 71-82 in WO 2005/003086].

In view of the drawbacks of the fluorescent dyes of the prior art, the main object of the present invention was to provide novel fluorescent dyes which would exhibit improved properties, namely photostability in aqueous solutions, hydrophilicity, high values for adsorption and emission maxima, recovery times of several tens—several hundreds of milliseconds, minimal content of the dye in the ground state after the pump pulse, the possibility of the enhanced recovery caused by the irradiation with the UV light, and which would be particularly suitable for microscopy applications with very high light intensities such as STED, FCS and GSDIM.

This object has been achieved by providing the novel rhodamines according to the invention.

DESCRIPTION OF THE INVENTION

The photostable rhodamines of the invention are represented by the general structural formulae I, ID, II and IID below which all comprise the same scaffold.

These novel fluorescent rhodamine compounds of the present invention exhibit a number of favourable characteristics:
a) excitability with 633/635 and/or 647/650 nm light;
b) emission of light at about 660 nm or longer wavelengths;
c) providing high fluorescence quantum yields in solution (under single molecule conditions and after bioconjugation);
d) low intersystem crossing rates;
e) relatively long (>3 ns) excited state lifetimes;
f) high photostability under the STED conditions (by depletion with very strong light of 750 nm), particularly in the presence of air-oxygen;
g) recovery times of ca. 50 ms, minimal content (ca. 3%) of the dye in the ground state after the pump pulse and the possibility of the enhanced recovery caused by the irradiation with the UV laser (375 nm);
h) the same fluorescent dye is available in a hydrophilic (soluble in water and aqueous buffers) and in a hydrophobic (insoluble in water or aqueous buffers) form (with the same chromophore) for binding with hydrophilic and lipophilic substrates, respectively;
i) various reactive sites for attaching to various functional groups may easily be introduced.

The novel rhodamine compounds of the present invention have the following general formula I:

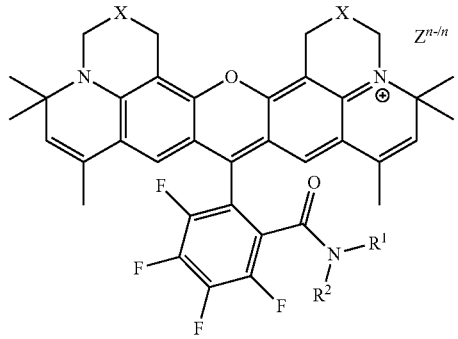

wherein
$R^1$=an unsubstituted or substituted alkyl group, including a cycloalkyl group, or heterocycloalkyl group;
$R^2$=H, an unsubstituted or substituted alkyl group, including a cycloalkyl group, or heterocycloalkyl group, or an unsubstituted or substituted aryl group or heteroaryl group, or any combination of such groups;
$X=CH_2$, $C=O$, $C=NOR^a$, $C=NNR^aNR^b$, $CH(OR^a)$, O, S, SO, $SO_2$, or any other derivatives of these groups, with $R^a$ and $R^b$ independently being H or an organic residue, in particular an unsubstituted or substituted (cyclo)alkyl group or heterocycloalkyl group, an unsubstituted or substituted aryl group or heteroaryl group;

Z=a negatively charged group with 1, 2, 3, 4 or 5 charges per anion.

A short straight line attached to a nitrogen or carbon atom in formula I above but also in any of the following formulae represents a methyl group (according to the common practice).

Specific, but not limiting examples for $R^1$ are an unsubstituted or substituted methyl group, ethyl group, lower (cyclo) alkyl group with 3-10 C atoms, or (cyclo)alkyl group with 11-30 or more C atoms.

The term "aryl", as used herein, refers to a mono-, bi- or tricyclic carbocyclic ring system having one, two or three aromatic rings including but not limited to phenyl, naphthyl, anthryl, azulyl, tetrahydronaphthyl, indanyl and indenyl.

The term "heteroaryl", as used herein, refers to a cyclic aromatic radical having from 5 to 10 ring atoms of which at least one ring atom is selected from S, O and N; the radical being joined to the rest of the molecule via any of the ring atoms. Representative, but not limiting examples are pyridinyl, pyrazinyl, pyrimidinyl, pyrrolyl, imidazolyl, thiazolyl, oxazolyl, isooxazolyl, thiadiazolyl, oxadiazolyl, thiophenyl, furanyl, quinolinyl and isoquinolinyl.

The term "heterocycloalkyl" as used herein, refers to a non-aromatic 3-, 4-, 5-, 6- or 7-membered ring or a bi- or tricyclic group comprising fused 6-membered rings having between 1 and 3 heteroatoms independently selected from S, O and N, including but not limited to pyrrolidinyl, pyrazolinyl, pyrazolidinyl, imidazolidinyl, piperidinyl, piperazinyl, oxazolidinyl, isoxazolidinyl, isooxazolidinyl, morpholinyl, thiazolidinyl, isothoazolidinyl, and tetrahydrofuryl.

Specific, but not limiting examples for $R^2$ are H, an unsubstituted or substituted methyl group, ethyl group, lower (cyclo)alkyl group with 3-10 C atoms, or a (cyclo)alkyl group with 11-30 or more C atoms, an unsubstituted or substituted phenyl, naphthyl, or anthryl group, or a pyridinyl, pyrazinyl, pyrimidinyl, pyrrolyl, imidazolyl, thiazolyl, oxazolyl, isooxazolyl, thiadiazolyl, oxadiazolyl, thiophenyl, furanyl, quinolinyl, isoquinolinyl, pyrrolidinyl, pyrazolinyl, pyrazolidinyl, imidazolidinyl, piperidinyl, piperazinyl, oxazolidinyl, isoxazolidinyl, isooxazolidinyl, morpholinyl, thiazolidinyl, isothoazolidinyl, or tetrahydrofuryl group. Preferably, $R^2$ is an unsubstituted or substituted (cyclo)alkyl group, in particular an unsubstituted or substituted methyl group, ethyl group, lower (cyclo)alkyl group with 3-10 C atoms, or a (cyclo)alkyl group with 11-30 or more C atoms.

In a more specific embodiment, $R^1$ in formula I is $-[CH_2]_n-COY$ with Y being F, Cl or Br, and n being an integer from 1 to 21, preferably from 1-8, more preferred from 2-6, and $R^2$ is an unsubstituted or substituted alkyl group, including a cycloalkyl group, e.g. an unsubstituted or substituted methyl group, ethyl group, lower (cyclo)alkyl group with 3-10 C atoms, or a (cyclo)alkyl group with 11-30 or more C atoms. $R^2$ may be in particular $-[CH_2]_n-COY$ as defined above for $R^1$. Especially preferred is $R^2$ a methyl or ethyl group. Preferably X is $CH_2$.

In a further specific embodiment, $R^1$ in formula I is $-[CH_2]_n-COOR^3$ with $R^3$ being H or an organic residue, in particular an unsubstituted or substituted alkyl group, including a cycloalkyl group, e.g. an unsubstituted or substituted methyl group, ethyl group, lower (cyclo)alkyl group with 3-10 C atoms, or a (cyclo)alkyl group with 11-30 or more C atoms, a heterocycloalkyl group, or an unsubstituted or substituted aryl group, heteroaryl group as defined above, or an imido group linked through its nitrogen atom, in particular an N-succinimidyl or N-(2-sulfosuccinimidyl) group, n being an integer from 1 to 21, preferably from 1-8, more preferred from 2-6, and $R^2$ is H or an unsubstituted or substituted alkyl group, including a cycloalkyl group, e.g. an unsubstituted or substituted methyl group, ethyl group, lower alkyl group with 3-10 C atoms, or a (cyclo)alkyl group with 11-30 or more C atoms. $R^2$ may be in particular $-[CH_2]_n-COOR^3$ as defined above for $R^1$. Especially preferred is $R^2$ a methyl or ethyl group. Preferably X is $CH_2$.

Still more specifically, the compound having the above general formula I is represented by one of the following formulae

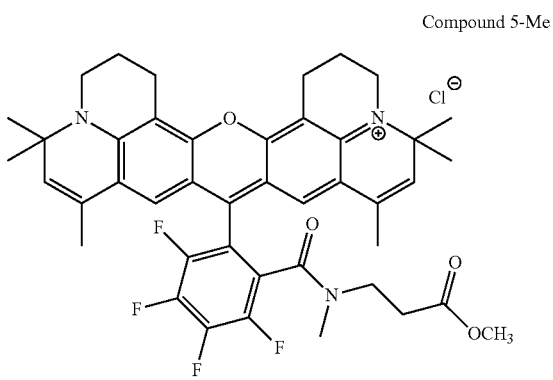

Compound 5-Me

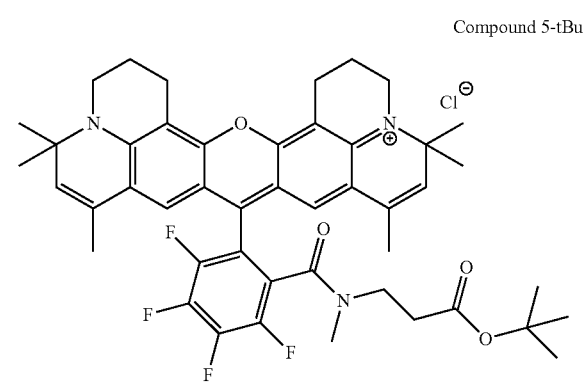

Compound 5-tBu

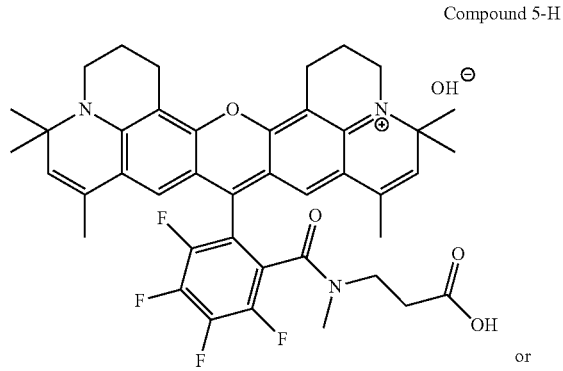

Compound 5-H or

-continued

Compound 8

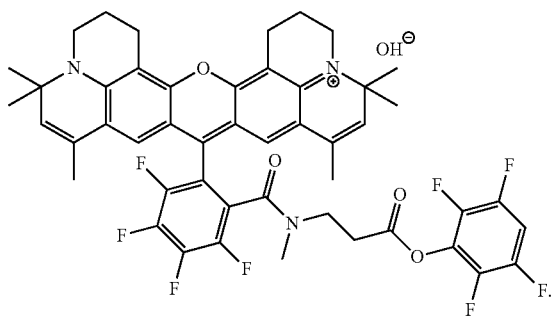

The novel rhodamine compounds of the present invention have the following general formula II:

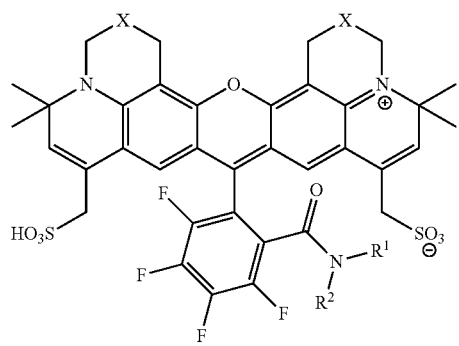

wherein

R$^1$=an unsubstituted or substituted alkyl group, including a cycloalkyl group, or heterocycloalkyl group;

R$^2$=H, an unsubstituted or substituted alkyl group, including a cycloalkyl group, or heterocycloalkyl group, an unsubstituted or substituted aryl group or heteroaryl group, or any combination of such groups;

X=CH$_2$, C=O, C=NOR$^a$, C=NNR$^a$NR$^b$, CH(OR$^a$), O, S, SO, SO$_2$, or any other derivatives of these groups, with R$^a$ and R$^b$ independently being H or an organic residue, in particular an unsubstituted or substituted (cyclo)alkyl group or heterocycloalkyl group, an unsubstituted or substituted aryl group or heteroaryl group.

Specific, but not limiting examples for R$^1$ are an unsubstituted or substituted methyl group, ethyl group, lower (cyclo)alkyl group with 3-10 C atoms, or a (cyclo)alkyl group with 11-30 or more C atoms.

The term "aryl", as used herein above, refers to a mono-, bi- or tricyclic carbocyclic ring system having one, two or three aromatic rings including but not limited to phenyl, naphthyl, anthryl, azulyl, tetrahydronaphthyl, indanyl and indenyl.

The term "heteroaryl", as used herein above, refers to a cyclic aromatic radical having from 5 to 10 ring atoms of which at least one ring atom is selected from S, O and N; the radical being joined to the rest of the molecule via any of the ring atoms. Representative, but not limiting examples are pyridinyl, pyrazinyl, pyrimidinyl, pyrrolyl, imidazolyl, thiazolyl, oxazolyl, isooxazolyl, thiadiazolyl, oxadiazolyl, thiophenyl, furanyl, quinolinyl and isoquinolinyl.

The term "heterocycloalkyl" as used herein above, refers to a non-aromatic 3-, 4-, 5-, 6- or 7-membered ring or a bi- or tricyclic group comprising fused 6-membered rings having between 1 and 3 heteroatoms independently selected from S, O and N, including but not limited to pyrrolidinyl, pyrazolinyl, pyrazolidinyl, imidazolidinyl, piperidinyl, piperazinyl, oxazolidinyl, isoxazolidinyl, isooxazolidinyl, morpholinyl, thiazolidinyl, isothiazolidinyl, and tetrahydrofuryl.

Specific, but not limiting examples for R$^2$ are H, an unsubstituted or substituted methyl group, ethyl group, lower (cyclo)alkyl group with 3-10 C atoms, or a (cyclo)alkyl group with 11-30 or more C atoms, an unsubstituted or substituted phenyl, naphthyl, anthryl, group or a pyridinyl, pyrazinyl, pyrimidinyl, pyrrolyl, imidazolyl, thiazolyl, oxazolyl, isooxazolyl, thiadiazolyl, oxadiazolyl, thiophenyl, furanyl, quinolinyl, isoquinolinyl, pyrrolidinyl, pyrazolinyl, pyrazolidinyl, imidazolidinyl, piperidinyl, piperazinyl, oxazolidinyl, isoxazolidinyl, isooxazolidinyl, morpholinyl, thiazolidinyl, isothiazolidinyl, or tetrahydrofuryl group. Preferably, R$^2$ is an unsubstituted or substituted (cyclo)alkyl group, in particular an unsubstituted or substituted methyl group, ethyl group, lower (cyclo)alkyl group with 3-10 C atoms, or a (cyclo)alkyl group with 11-30 or more C atoms.

In a specific embodiment, R$^1$ in formula II is —[CH$_2$]$_n$—COOR$^3$ with R$^3$ being H or an organic residue, in particular an unsubstituted or substituted alkyl group, including a cycloalkyl group, or heterocycloalkyl group, an unsubstituted or substituted aryl group or heteroaryl group as defined above, or an N-linked imido group, or R$^1$ is a —[CH$_2$]$_n$—R$^4$ group with R$^4$ being an N-linked maleimido group or a —S—S—R$^5$ group with R$^5$ being an organic residue, in particular an unsubstituted or substituted alkyl group, including a cycloalkyl group, or heterocycloalkyl group, an unsubstituted or substituted aryl group or heteroaryl group as defined above, n is an integer from 1 to 21, and R$^2$ is H or an unsubstituted or substituted (cyclo)alkyl group, in particular an unsubstituted or substituted methyl group, ethyl group, lower (cyclo)alkyl group with 3-10 C atoms, or a (cyclo)alkyl group with 11-30 or more C atoms, or a heterocycloalkyl group. R$^2$ may in particular be —[CH$_2$]$_n$—COOR$^3$ or —[CH$_2$]$_n$—R$^4$ as defined above for R$^1$. Especially preferred is R$^2$ a methyl or ethyl group. Preferably X is CH$_2$.

Still more specifically, the compound having the above general formula II is represented by one of the following formulae Compound 6

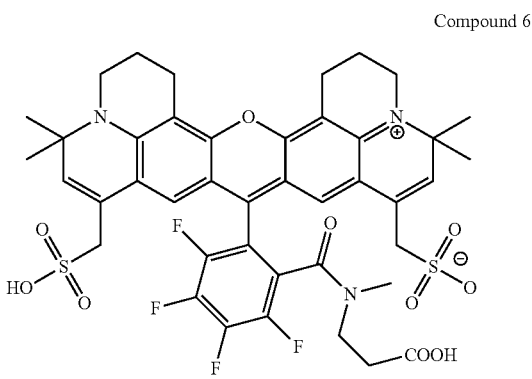

Compound 9

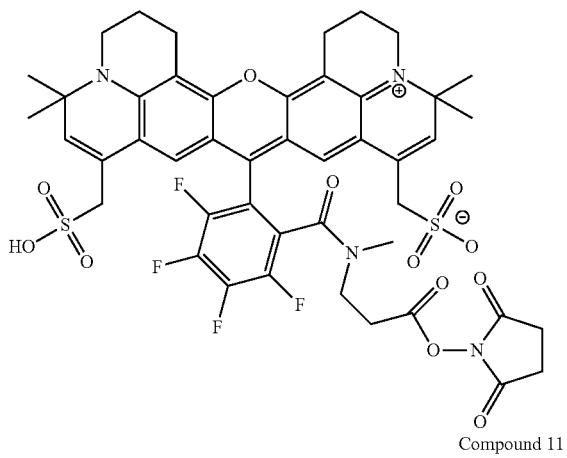

Compound 11

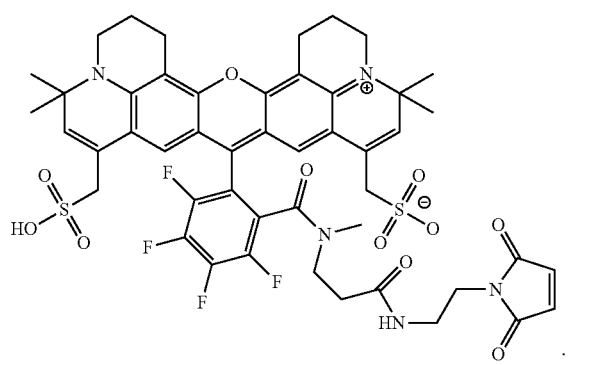

Another aspect of the present invention relates to compounds of the above general formulae I or II having more than 2 atoms of H, C or N replaced by their stable isotopes ($^2$H, $^{13}$C and $^{15}$N).

A more specific embodiment of this aspect of the present invention are compounds of the following general formula ID:

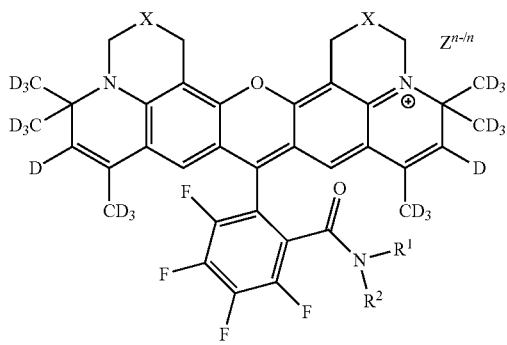

wherein
R$^1$=an unsubstituted or substituted alkyl group, including a cycloalkyl group, or heterocycloalkyl group;
R$^2$=H, an unsubstituted or substituted alkyl group, including a cycloalkyl group, or heterocycloalkyl group, an unsubstituted or substituted aryl group or heteroaryl group, or any combination of such groups;
X=CH$_2$, C=O, C=NOR$^a$, C=NNR$^a$NR$^b$, CH(OR$^a$), O, S, SO, SO$_2$, or any other derivatives of these groups, with R$^a$ and R$^b$ independently being H or an organic residue, in particular an unsubstituted or substituted (cyclo)alkyl group or heterocycloalkyl group, an unsubstituted or substituted aryl group or heteroaryl groups;
Z=a negatively charged group with 1, 2, 3, 4 or 5 charges per anion;
having 16-18 randomly distributed deuterium atoms in all positions denoted CD or CD$_3$.

In a more specific embodiment, R$^1$ is —[CH$_2$]$_n$—COY with Y being F, Cl or Br, and n being an integer from 1 to 21, or —[CH$_2$]$_n$—COOR$^3$ with R$^3$ being H or an organic residue, in particular an unsubstituted or substituted alkyl group, including a cycloalkyl group, an unsubstituted or substituted aryl group or heteroaryl group, or an N-linked imido group, n being an integer from 1 to 21, and R$^2$ is H or an unsubstituted or substituted alkyl group, including a cycloalkyl group, in particular an unsubstituted or substituted methyl group, ethyl group, lower (cyclo)alkyl group with 3-10 C atoms, or a (cyclo)alkyl group with 11-30 or more C atoms, or a heterocycloalkyl group. R$^2$ may be in particular —[CH$_2$]$_n$—COY or —[CH$_2$]$_n$—COOR$^3$ as defined above for R$^1$. Especially preferred is R$^2$ a methyl or ethyl group. Preferably X is CH$_2$.

A further specific embodiment of this aspect of the present invention are compounds of the following general formula IID:

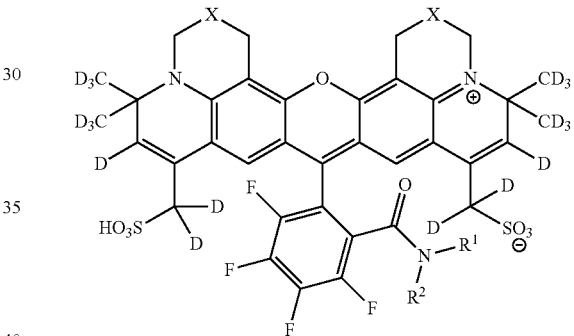

wherein
R$^1$=an unsubstituted or substituted alkyl group, including a cycloalkyl group, or heterocycloalkyl group;
R$^2$=H, an unsubstituted or substituted alkyl group, including a cycloalkyl group, or heterocycloalkyl group, an unsubstituted or substituted aryl group or heteroaryl group, or any combination of such groups;
X=CH$_2$, C=O, C=NOR$^a$, C=NNR$^a$NR$^b$, CH(OR$^a$), O, S, SO, SO$_2$, or any other derivatives of these groups, with R$^a$ and R$^b$ independently being H or an organic residue, in particular an unsubstituted or substituted (cyclo)alkyl group or heterocycloalkyl group, an unsubstituted or substituted aryl group or heteroaryl group;
having 16-18 randomly distributed deuterium atoms in all positions denoted CD or CD$_3$.

More specifically, R$^1$ is —[CH$_2$]$_n$—COOR$^3$ with R$^3$ being H or an organic residue, in particular an unsubstituted or substituted (cyclo)alkyl group or heterocycloalkyl group, an unsubstituted or substituted aryl group or heteroaryl group, or an N-linked imido group, or R$^1$ is a —[CH$_2$]$_n$—R$^4$ group with R$^4$ being an N-linked maleimido group or a —S—S—R$^5$ group with R$^5$ being an organic residue, in particular an unsubstituted or substituted (cyclo)alkyl group or heterocycloalkyl group, an unsubstituted or substituted aryl group or heteroaryl group, n is an integer from 1 to 21, and R$^2$ is an unsubstituted or substituted (cyclo)alkyl group or heterocycloalkyl group, in particular an unsubstituted or substituted methyl group, ethyl group, lower (cyclo)alkyl group with 3-10 C atoms, or a (cyclo)alkyl group with 11-30 or more C atoms. $R^2$ may be in particular —[CH$_2$]$_n$—COOR$^3$ or —[CH$_2$]$_n$—R$^4$ as defined above for $R^1$. Especially preferred is $R^2$ a methyl or ethyl group. Preferably X is CH$_2$.

Still more specifically, the compound having the above general formula IID is represented by one of the following formulae:

Compound 6D

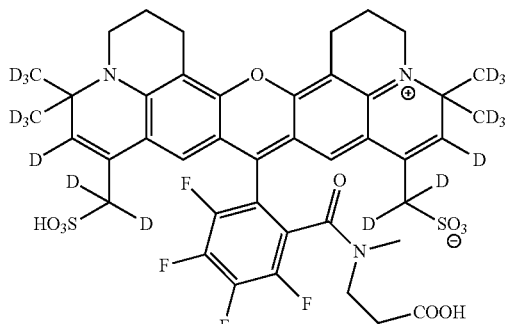

Compound 9D

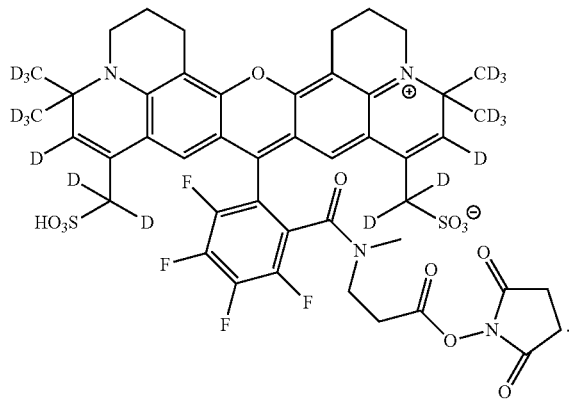

A further aspect of the invention relates to various advantageous uses of the present compounds of the structural formulae I, II, ID, and IID. Due to their favourable characteristics, these compounds represent efficient fluorescent dyes and markers. The new fluorescent dyes emit light at about 660 nm, possess high values of the fluorescence quantum yields in solution (up to 80%), relatively long excited state lifetimes (>3 ns), are resistant against photobleaching under STED conditions (with depletion at 750 nm) in the presence of air-oxygen and exhibit relatively low rates of intersystem crossing. In particular, they perform very well in conventional and stimulated emission depletion (STED) microscopy and fluorescence correlation spectroscopy, especially with very high light intensities. They possess advantageous GSD parameters, such as recovery times of ca. 50 ms, very low content of the dye in the ground state after the pump pulse (ca. 3%), and their recovery to the fluorescent ground state may be enhanced by the irradiation with the UV laser (375 nm). Moreover, these compounds as such or after introduction of reactive sites such as amino or thio functional groups or other suitable groups known in the art can be readily coupled to other molecules, in particular biomolecules such as peptides, proteins, lipids, carbohydrates, nucleic acids, or toxins, and the resulting bioconjugates can be used as fluorescent dyes or markers as well.

Thus, the present invention provides the use of compounds according to the invention or any of their stable conjugates with biomolecules or any other chemical substances such as peptides, proteins, lipids, carbohydrates, nucleic acids, toxins, etc. as fluorescent dyes. More specifically, the present invention provides the use thereof in the fields of spectroscopy or microscopy, such as reversible saturable optically linear fluorescent transitions microscopy, in particular stimulated emission depletion microscopy, fluorescence correlation spectroscopy, ground state depletion method, or conventional microscopy.

The present invention also provides the use of hydrophilic compounds in free form or attached to antibodies or other biomolecules for microinjections into cells and for immunostaining applications. As demonstrated with the exemplary compounds 6/6D and 9/9D, respectively, in Example 5, their conjugates with antibodies produce a very low background in immunostaining experiments due to the low affinity of the dyes to intracellular components.

As already indicated above, an important aspect of the present invention resides in providing stable isotopic derivatives of the compounds of general formulae I and II. Such isotopic derivatives may be used as molecular mass distribution tags in various mass spectrometry applications, e.g. for identification and quantification of various substance classes (e.g. amines and thiols), in a complex mixture, and may also provide advantages in spectroscopic properties of bioconjugates, such as a reduction of the rate of non-radiative deactivation, improvement of the fluorescent quantum yield and diagnostically important changes in the excited states lifetimes.

A specific and preferred embodiment of this aspect of the invention is the use of compounds according to the invention having the general formulae ID or IID as defined above with 16-18 randomly distributed deuterium atoms in all positions denoted CD, CD$_2$ or CD$_3$, having a narrow and symmetrical molecular mass distribution, as molecular mass distribution tags in mass spectrometry, two-dimensional mass spectrometry (MS-MS) or in any combination of mass spectrometry with chromatography or any other separation technique, in particular gel filtration chromatography, electrophoresis, e.g. poly(acrylamide) gel electrophoresis, ion exchange chromatography etc.

In a further specific aspect, the present invention also provides improved methods for producing compounds of the general formulae I or II wherein $R^1$ is —[CH$_2$]$_n$—COOH. These methods involves the use of t-butyl esters of general formula I as defined above, wherein $R^1$ is —[CH$_2$]$_n$—COOtBu, particularly compound 5-tBu, as advantageous direct precursors for facile one-step preparation of the sulfonated water-soluble compounds of general formula II, wherein $R^1$ is —[CH$_2$]$_n$—COOH, and for facile one-step preparation of the lipophilic compounds of general formula I, wherein $R^1$ is —[CH$_2$]$_n$—COOH. In the first preparation method, the t-butyl ester is treated with sulfuric acid (H$_2$SO$_4$) or other sulfonating reagents, e.g. SO$_3$, SO$_3$ in H$_2$SO$_4$, SO$_2$Cl$_2$, etc. In the second preparation method, the t-butyl ester is treated with hydrogen chloride or other acidic reagents in suitable solvents such as dioxane, ethyl acetate, diethyl ether, water, etc. As demonstrated with the exemplary compound 5-tBu, it can be easily converted either to the lipophilic compound 5-H or to the hydrophilic compound 6 in one step with excellent yields.

General Synthesis and Spectral Properties of the Novel Fluorescent Dyes

Preparation of the lipophilic fluorescent dyes 5-R started with compound 1, which was synthesized from m-anisidine

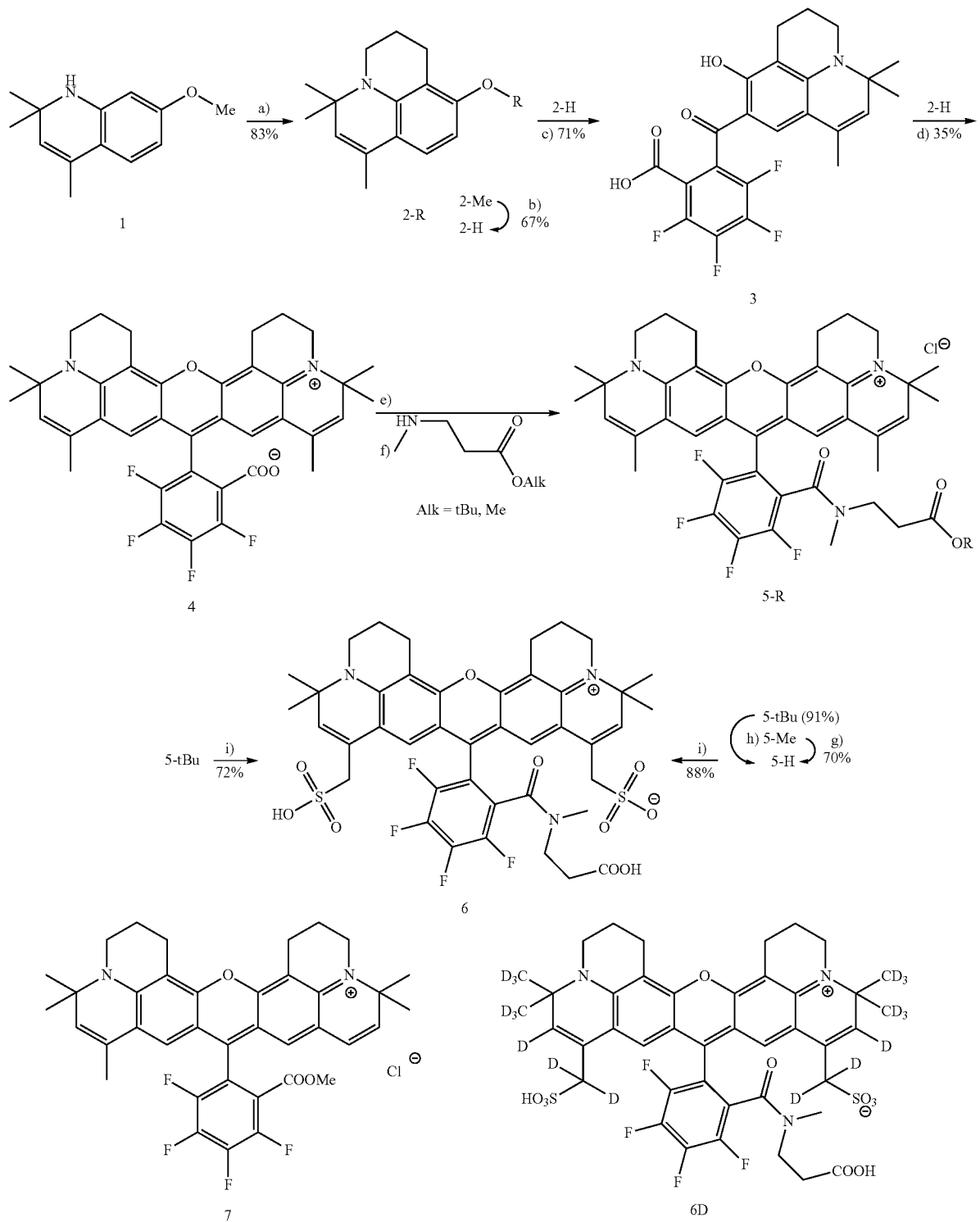

Scheme 1.

Synthesis of the lipophilic (5, 7) and hydrophilic (6) rhodamines: a) Br(CH$_2$)$_3$Cl, Na$_2$CO$_3$, KI, CH$_3$CN, reflux, 25 h; b) 48% aq. HBr, glacial AcOH, 135-140° C., 22 h; c) tetra-fluorophthalic anhydride, toluene, reflux, 5 h; d) POCl$_3$, ClCH$_2$CH$_2$Cl, 63-65° C., 3.5 h; e) POCl$_3$, ClCH$_2$CH$_2$Cl, reflux, 2.5 h; f) Et$_3$N, CH$_3$CN, room temp.; g) 10% aq. KOH, THF, 0° C.; h) 2M HCl in 1,4-dioxane, room temp.; i) 96-98% H$_2$SO$_4$, room temp., 40 h.

and acetone in the presence of ytterbium(III) triflate according to the general method described by L. A. Robinson and M. E. Theoclitou [*Tetrahedron Lett.* 2002, 43, 3907-3910; cf.: C. S. Yi, S. Y. Yun, *J. Amer. Chem. Soc.* 2005, 127, 17000-17006]. The alkylation of compound 1 with 1-bromo-3-chloropropane was carried similarly to the procedure described in U.S. Pat. No. 6,372,907 for its closest analogue, the corresponding 10-pivaloyl ester. Demethylation of the tricyclic ether 2-Me was carried out under conditions reported for the aromatic methyl esters by R. Hermann, H.-P. Josel, K.-H. Drexhage and J. Arden-Jacob [(Boehringer Mannheim GmbH) U.S. Pat. No. 5,755,0409 (12 May 1998)]. Conversion of the compound 2-H into the rhodamine 4 was performed stepwise according to the known method used for, the synthesis of the asymmetric xanthene derivatives. In methanol, the absorption and emission maxima of rhodamine 4 were observed at 616 and 641 nm, respectively. Condensation of the compounds 3 and 2-H affords the corresponding acid chloride as an intermediate. Aqueous work-up leads to the zwitterionic substance 4, while quenching the reaction with methanol produces the methyl ester 7 in 46% yield. Other esters of the rhodamine 4 may easily be obtained in a similar way.

High frequency C—H stretch vibrations ($\nu \approx 3000$ cm$^{-1}$) considerably contribute to the non-radiative $S_1 \rightarrow S_0$ transition characterized by the Frank-Condon factor ($f_0$), which is associated with the maximum possible rate of the non-emissive decay ($f_0 \approx 1013$ s$^{-1}$ in most chromophores with C—H bonds) (e.g. M. J. Frampton, G. Accorsi, N. Armaroli, J. E. Rogers, P. A. Fleitz, K. J. McEwan and H. L. Anderson, *Org. Biomol. Chem.*, 2007, 5, 1056-1061). Therefore, isotopic substitution which creates C-D bonds with considerably lower vibrational energy ($\nu \approx 2200$ cm$^{-1}$) may reduce the rate of non-radiative deactivation, improve the fluorescent quantum yield and prolong the excited states lifetimes. These effects are likely to be observed in rigid molecular systems (e.g. rhodamines), where the $S_1$ and $S_0$ states are known to have very similar geometries, so that their potential energy surfaces do not intersect. Consequently, the overall deactivation rate may be approximated by the internal conversion, which is determined by the Frank-Condon factor. Also, deuterated and non-deuterated fluorophores with the same structure are expected to have the same (or nearly the same) intersystem crossing rates ($S_1 \rightarrow T_1$). In view of all these factors, the present inventors suspected that deuteration might increase the values of the fluorescent quantum yield and the excited state lifetimes. Therefore, the deuterated analogue of the fluorescent dye 6 (compound 6D) was prepared and compared with the parent compound with respect to their spectra, the values of the fluorescent quantum yields in a free state and after conjugation with the antibodies, and the lifetimes of the excited states (Table 2). Compound 6D was synthesized similarly to the compound 6. Only a very large excess of acetone-$d_6$ in the reaction with m-anisidine catalysed by the anhydrous ytterbium(III) triflate affords the compound 1-Me with a sufficiently high deuterium content. The structural fragment C(CD$_3$)=CD in the compound 1-Me is especially prone to the D-H exchange. Therefore, the subsequent alkylation with Br(CH$_2$)$_3$Cl was performed in acetonitrile-$d_3$ in the presence of Na$_2$CO$_3$ (instead of NaHCO$_3$). Cleavage of the deuterated methyl ester 2-Me was performed using 48% DBr in D$_2$O mixed with AcOD. Other steps leading to the compound 5-tBu did not involve reagents or solvents with easily exchangeable protons and were performed as for the undeuterated precursor. Advantageously, the reaction with 97% D$_2$SO$_4$ in D$_2$O substantially improved the deuteration degree in the fragment C(CD$_3$)=CD so that the final compound 6D displayed a very narrow molecular mass distribution with two highest peaks corresponding to the presence of 17 and 18 D-atoms (of 18 possible).

The bifunctional β-alanine "bridge" was attached to the carboxy group in compound 4 and its deuterated analogue following the technique developed as a result of previous research of the inventors [V. P. Boyarskiy, V. N. Belov, R. Medda, B. Hein, M. Bossi, S. W. Hell, *Chem. Eur. J.* 2008, 14, 1784-1792]. It was established that the utilization of N-methyl-β-alanine tert-butyl ester instead of the methyl ester demonstrates certain advantages. In contrast to n-alkyl esters, tert-butyl esters are easily cleaved under acidic conditions. Thus, in our synthesis of the sulfonated water-soluble hydrophilic dye 6 the subsequent alkali-assisted saponification step becomes unnecessary. The absence of this step not only shortens the reaction sequence, but also prevents the undesired fluorine substitution in the aromatic ring in dye 6. (Under basic conditions in methanol one of the four fluorine atoms might be substituted with a strongly nucleophilic methoxide or hydroxide anions.) Also importantly, the same starting material—tert-butyl ester 5-tBu—can be smoothly converted to the corresponding carboxylic acid 5-H by simple treatment with 2 M HCl in 1,4-dioxane. In fact, the non-sulfonated compound. 5-H represents the required lipophilic analogue of rhodamine 6. Later the inventors managed to saponificate the methyl ester 5-Me into the carboxylic acid 5-H, using an excess of a highly diluted aq. KOH solution at room temperature. The absence of methanol in the reaction mixture was crucial; with methanol, the saponification reaction invariably gave unseparable mixtures of 5-H and an unidentified substance with the close retention parameters both on silica gel and the reversed phase. Finally, mixing of the ester 5-tBu or the acid 5-H with a large excess of 96-98% H$_2$SO$_4$ at 0° C. followed by keeping the reaction solution at room temperature afforded the desired hydrophilic fluorescent dye 6. Fortunately, these drastic conditions left the secondary amido group intact. The solubility of the compound 6-H in water is high: up to 40-45 mg of it may easily be dissolved in 1 mL of water at room temperature. The dark-blue aqueous solutions produce intense dark-red fluorescence when irradiated with incandescent or halogen lamps. Unlike compounds 6 and 6D, the lipophilic rhodamine 5 is very poorly soluble in water, and its $\Phi_{fl}$-value in aqueous solution is lower than that of the disulphonic acid 6 (Table 2). On the contrary, the solubility of the dye 5-H in DMF, THF or even CHCl$_3$ is very good. Due to the presence of the asymmetrically substituted secondary amide fragment, molecules of the compounds 5 and 6 (and their derivatives; see Scheme 1) possess an N—C chirality axis. Rotational barrier in asymmetrically substituted tertially amides is high enough (ca. 18 kcal/mol), and in the NMR spectra two signals of the N-methyl group are observed (in ca. 1:2-1:3 ratio). The presence of the chirality axis makes the "opposite" methyl groups and the CH-atoms attached to the "left" and "right" sides of the xanthene fragment to be non-equivalent (diastereotopic), and in the NMR spectra of the compounds 5 and 6 two additional sets of equally strong signals may be observed. For example, four signals of the methyl groups at the double C=C bond are found in $^1$H NMR spectra of the esters 5-Me and 5-tBu (see Examples for the NMR data).

TABLE 2

Properties of the fluorescent dyes of the invention prepared as outlined above.*

| Compound | $\lambda_{max}$ (abs.) nm | $\lambda_{max}$ (fl.) nm | Solvent | $\epsilon \cdot 10^{-5}$ $M^{-1}$ $cm^{-1}$ | $\Phi_{fl}$ % in water[19] | $\tau_{fl}$ ns | Solubility (polarity) |
|---|---|---|---|---|---|---|---|
| 4 | 616 | 641 | MeOH | | 63 | | $CHCl_3$, THF; non-polar |
| 7 | 632 | 655.5 | MeOH | | | | $CHCl_3$, THF; non-polar |
| 5-tBu | 638 | 661 | MeOH | 0.92 | 61 | | DMF, THF, $CHCl_3$; non-polar |
| 5-Me | 638 | 661.5 | MeOH | 0.66 | 62 | | DMF, THF, $CHCl_3$; non-polar |
| 5-H | 638 | 661.5 | MeOH | 0.73 | 53 | | DMF, THF, $CHCl_3$; non-polar |
| 6 | 637 | 660 | $H_2O$ | 0.94 | 80 | 3.57[20] | >0.1M in $H_2O$; polar, hydrophilic |
| 6D | 637 | 660 | $H_2O$ | 0.92 | 78 | 3.67[21] | >0.1M in $H_2O$; polar, hydrophilic |

*See Table 1 for definitions of $\lambda_{max}$ (abs.), $\lambda_{max}$ (fl.), $\epsilon$ and $\tau_{fl}$.
[19] Atto 633 was used as a reference ($\Phi_{fl}$ = 64% in aqueous buffer).
[20] Intersystem crossing rate ($k_{ISC}$) = 2.5 ± 0.15 × $10^6$ $s^{-1}$; rate of the $T_1 \to S_0$ transition ($k_T$) = 2.71 × $10^5$ $s^{-1}$ ($H_2O$, 25° C., FCS study under single molecule conditions)
[21] Intersystem crossing rate ($k_{ISC}$) = 2.6 ± 0.2 × $10^6$ $s^{-1}$; rate of the $T_1 \to S_0$ transition ($k_T$) = 2.89 × $10^5$ $s^{-1}$ ($H_2O$, 25° C., FCS study under single molecule conditions)

Spectroscopic properties of the fluorescent dyes 5-7 are given in Table 2. The required absorption and emission parameters of the lipophilic (5-H) and hydrophilic (6 and 6D) fluorescent dyes have been successfully achieved. The absorption and emission maxima are found to be in-between the corresponding values of Alexa 633 and Atto 647N (Table 1). The Stokes shift (23 nm) is considerably larger that that of Alexa 633 and similar to the Stokes shift of Atto 647N (25 nm).

Fluorescence quantum yields of the dyes 6 and 6D were found to be practically equal (80 and 78%, respectively; compared with Atto 633 taken as a reference compound). This result was confirmed by comparison of the quantum yields of 6 and 6D with each other: they turned to be the same. Moreover, intersystem crossing rates ($k_{ISC}$) and rates of the $T_1 \to S_0$ transitions were also found to be the same for both deuterated and undeuterated substances (see ref. to Table 2). Isotopic substitution did not change any photophysical property of the dye 6D (in comparison with the unlabelled counterpart 6).

Dissolution of compounds 6 and 6D in methanol, aqueous methanol or methanol-containing mixtures is accompanied by the rapid esterification of the β-alanine fragment with methanol. Probably, the close proximity of the sulfonic acid residues to the carboxy group assists nucleophilic addition in these compounds due to the intramolecular acid catalysis. The sulfonic acid residues in rhodamines 6/6D prevent aggregation of the dye molecules in water or aqueous buffers. Therefore, these dyes are free from some drawbacks of Atto 647N mentioned above. Compounds 6/6D, which absorb and emit at 637 and 660 nm, respectively, may be also favourably compared with the Alexa 633 dye. The latter has a smaller Stokes shift (15 nm) and its absorption band with a maximum at 632 nm does not perfectly match the He—Ne red laser light (633 nm) or the 635 nm spectral line of red diode lasers. To demonstrate the applicability and performance of the new fluorescent dyes in bioconjugation experiments and microscopy, it was necessary first to prepare the reactive derivatives of the dyes 6/6D (and their lipophilic counterpart 5-H for comparison).

Scheme 2.

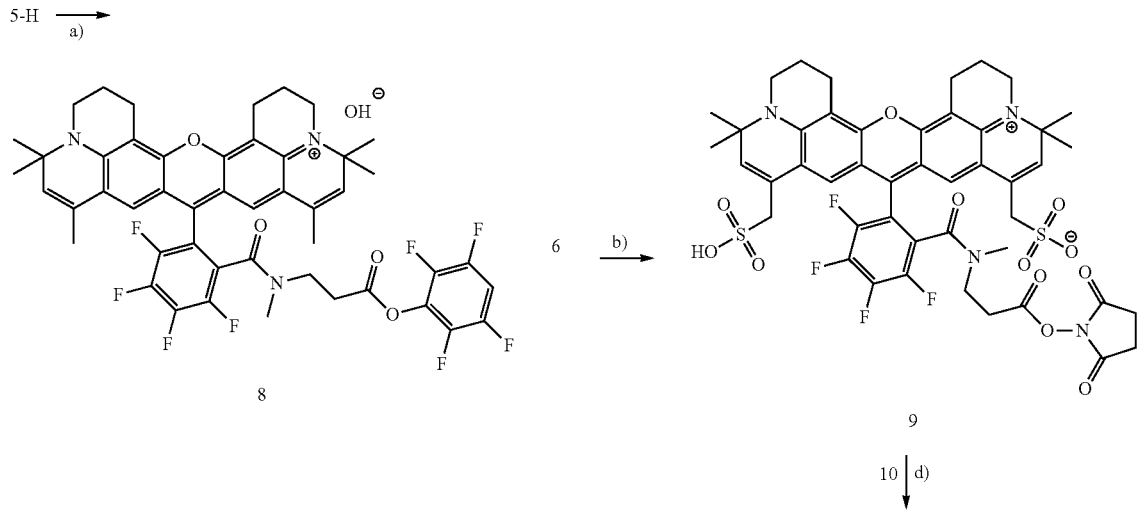

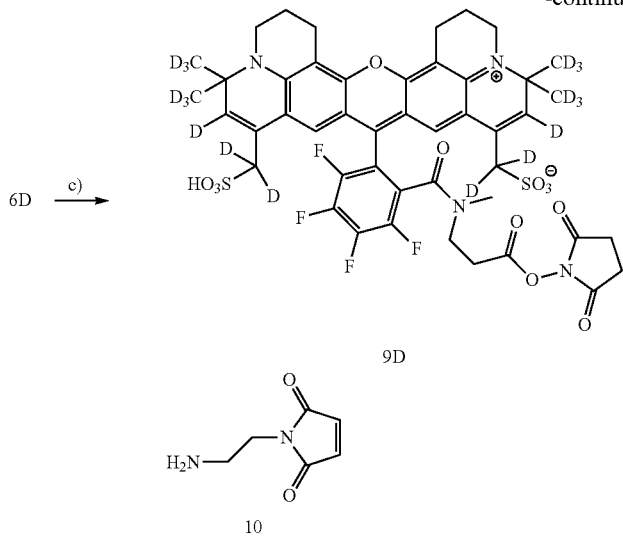
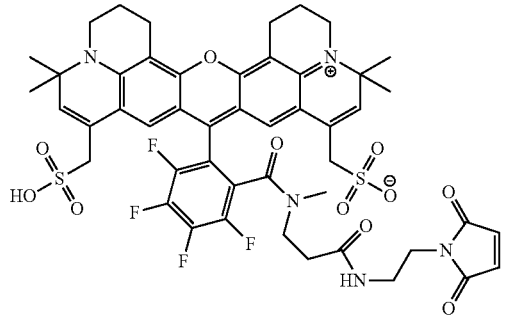

Synthesis of the reactive derivatives 8, 9 and 11 of the lipophilic (5-H) and hydrophilic (6/6D) rhodaminic dyes: a) 2,3,5,6-tetrafluorophenol, N-ethyl-N'-(3-dimethyl-aminopropyl)carbodiimide (EDC), CH₃CN, room temp.; b) N,N,N',N'-tetramethyl-O-(N-succinimidyl)uronium tetra-fluoro-borate (TSTU), Et₃N, DMF, room temp.; c) O-(7-aza-benzotriazol-1-yl)-N,N,N',N'-tetramethyluronium•hexafluoro-phosphate (HATU), DMF, Et₃N, room temp.; d) 10*CF₃COOH, DMF, Et₃N, room temp.

Usually, amino- or thiol reactive derivatives of the fluorescent dyes are used for labelling of proteins. For conjugation with amines, the free carboxy group needs to be activated by the formation of N-hydroxy(sulfo)succinimidyl esters, phenyl esters with electron-acceptor groups in the benzene ring or similar compounds with good leaving groups. The corresponding N-hydroxysuccinimide ester of lipophilic rhodamine 5-H proved to be extremely unstable, and tetrafluorophenyl ester (8) was prepared instead. Ester 8 partly decomposed in the course of chromatographic isolation using silica gel. Therefore, the reaction mixture containing the active ester 8 was used for labelling the lipids in their nonpolar domain and other coupling procedures. Low chemical stability of the ester 8 and the corresponding NHS derivative may be explained by the presence of the nucleophilic hydroxide group as a counter ion. The negatively charged OH⁻ ion is invariably formed at the first step of any esterification of the carboxy group in 5-H. If it could be exchanged quickly and under mild conditions to another, less nucleophilic anion (e.g. perchlorate) before the work-up of the reaction mixture, then the chances to isolate the final ester 8 (or the corresponding NHS ester) in a pure state would have been better. The NHS esters of the hydrophilic rhodamines 6 and 6D—compounds 9 and 10—turned out to be remarkably stable. They were isolated by reversed-phase HPLC using the gradient elution with aqueous acetonitrile with 0.1% (v/v) of TFA, lyophilized and stored at −20° C. under argon. Under these conditions, the content of the corresponding acids 6/6D in the very light dark blue voluminous solids increased from 3-5% up to 7-10% in 2 months. The higher stability of the NHS esters 9 and 10 may be explained by the absence of any nucleophilic counter ion. The maleimide derivative 11 has been prepared straight from compounds 9 and 10 by combining them in DMF with Et₃N as base. It was also isolated by HPLC. Importantly, the maleimide cycle in 11 turned out to be sensitive to methanol even at room temperature (e.g. by dissolving the sample in methanol during the mass-spectroscopic probe preparation).

The invention is further illustrated by the following non-limiting Examples and Figures.

INSTRUMENTS AND GENERAL PARAMETERS OF THE DETECTION METHODS USED

Figure 1:
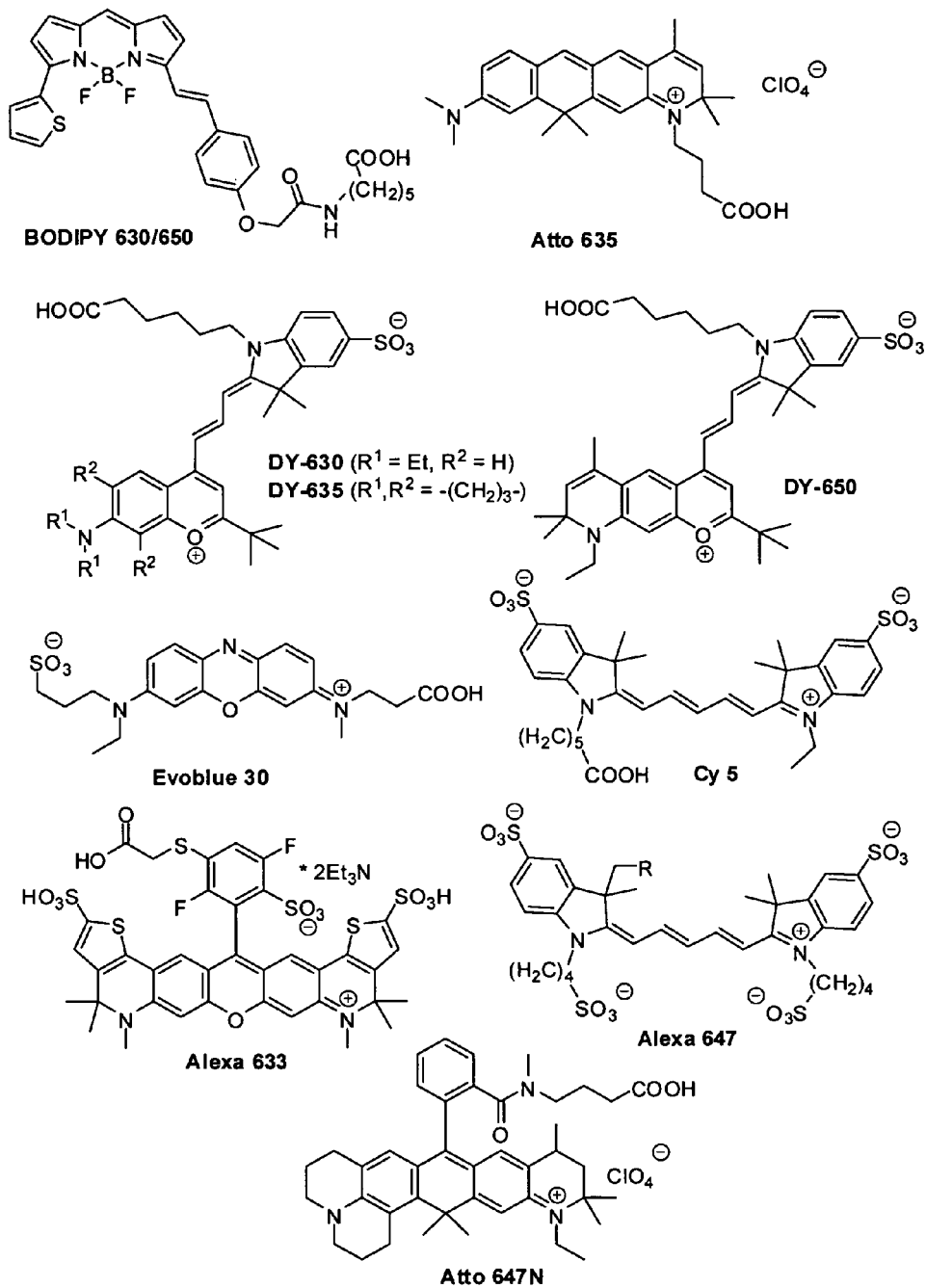
FIG. 1. Structures of the commercially available fluorescent dyes which may be excited with He—Ne red laser (633 nm) or the 635 nm spectral line of red diode lasers.

UV-visible absorption spectra were recorded on a Varian Cary 4000 UV-Vis spectrophotometer, and fluorescence spectra on a Varian Cary Eclipse fluorescence spectrophotometer. Reactions were carried out upon magnetic stirring in Schlenk flasks equipped with septa or reflux condensers with bubble-counters under argon using a standard manifold with vacuum and argon lines. All NMR spectra are referenced to tetramethylsilane as an internal standard (δ=0 ppm) using the signals of the residual protons of CHCl₃ (7.26 ppm) in CDCl₃, CHD₂OD (3.31 ppm) in CD₃OD, HOD (4.75 ppm) in D₂O,

[D$_5$]acetone (2.04 ppm) in [D$_6$]acetone or [D$_5$]DMSO (2.50 ppm) in [D$_6$]DMSO. Multiplicities of signals are described as follows: s=singlet, br. s=broad singlet, d=doublet, t=triplet, q=quartet, quint=quintet, m=multiplet, m$_c$=centrosymmetrical multiplet. Coupling constants (J) are given in Hz. Multiplicities in the $^{13}$C NMR spectra were determined by APT (Attached Proton Test) measurements. Low resolution mass spectra (electro spray ionization, ESI) were obtained with LCQ and ESI-TOF mass-spectrometers (MICROTOF (focus), Fa. Bruker). The MICROTOF spectrometer equipped with ESI ion source Apollo and direct injector with LC autosampler Agilent RR 1200 was used for obtaining high resolution mass spectra (ESI-HRMS). ESI-HRMS were obtained also on APEX IV spectrometer (Bruker). HPLC system (Knauer): Smartline pump 1000 (2×), UV detector 2500, column thermostat 4000 (25° C.), mixing chamber, injection valve with 20 and 100 μL loop for the analytical and preparative columns, respectively; 6-port-3-channel switching valve; analytical column: Eurospher-100 C18, 5 μm, 250×4 mm, 1.1 mL/min; preparative column: Eurospher-100-5 C18, 5 μm, 250×8 mm, 3.7 mL/min; solvent A: water+0.1% v/v trifluoroacetic acid (TFA); solvent B: MeCN+0.1% v/v TFA; detection at 636 nm (if not stated otherwise). Normal phase analytical TLC was performed on MERCK ready-to-use plates with silica gel 60 (F$_{254}$) and reversed phase TLC—on RP-18W/UV$_{254}$ precoated TLC plates (Macherey-Nagel). Preparative TLC was performed on MERCK HPTLC silica gel 60 plates (10×10 cm, layer thickness 0.2 mm). Column chromatography: MERCK silica gel, grade 60, 0.04-0.063 mm or Polygoprep 60-50 C18 (Macherey-Nagel).

Example 1

Synthesis of Specific Rhodamine Compounds

10-Methoxy-5,5,7-trimethyl-2,3-dihydro-1H,5H-pyrido[3,2,1-ij]quinoline (2-Me)

The alkylation of compound 1 with 1-bromo-3-chloropropane was carried out similarly to the procedure described in U.S. Pat. No. 6,372,907 for its closest analog, the corresponding 10-pivaloyl ester. To a solution of compound 1 (2.71 g, 13 mmol) and 1-bromo-3-chloropropane (8.32 g, 53 mmol) in CH$_3$CN (45 mL), the finely ground powders of NaHCO$_3$ (2.18 g, 26 mmol) and KI (17.3 g, 0.104 mol) were added, and the mixture was refluxed for 25 h with vigorous stirring. The solids were filtered off at room temperature and washed with CH$_2$Cl$_2$ (2☐60 mL). The organic solutions were combined, washed with water (2☐100 mL), dried and evaporated in vacuo. The residue was separated over a column with silica gel (100 g) using a hexane/CH$_2$Cl$_2$ (4:1) mixture as a mobile phase. The main fraction was evaporated in vacuo to afford 2.64 g (83%) of compound 2-Me as colorless crystals with m.p. 87-88° C. $^1$H NMR (300 MHz, CDCl$_3$): δ=1.28 (s, 6H), 1.90 (quint, $^3J_{H,H}$=6 Hz, 2H), 1.94 (br. s, 3H), 2.62 (t, $^3J_{H,H}$=6.5, 2H), 3.23 (t, $^3J_{H,H}$=5.6, 2H), 3.78 (s, 3H), 5.15 (br. s, 1H), 6.16 (d, $^3J_{H,H}$=8.6, 1H), 6.87 (d, $^3J_{H,H}$=8.6, 1H) ppm; $^{13}$C NMR (75.5 MHz, CDCl$_3$): δ 18.7 (Me), 21.4 (CH$_2$), 21.5 (CH$_2$), 26.7 (Me×2), 41.5 (CH$_2$), 55.2 (MeO), 55.8 (C), 97.8 (CH), 109.9 (C), 116.5 (C), 121.5 (CH), 127.4 (CH), 128.1 (C), 142.3 (C), 157.2 (C) ppm; EI-MS: m/z=243 (8) [M$^+$.], 228 (100) [M-Me]$^+$ 1,3,3-Trimethyl-6,7-dihydro-3H,5H-pyrido[3,2,1-ij]quinolin-8-ol (2-H)

Compound 2-Me (2.43 g, 10.0 mmol) was dissolved in a mixture of glacial AcOH (9 mL) and 48 aq. % HBr (9 mL), the solution was transferred into to a Schlenk flask with a magnetic stirring bar and a reflux condenser, stirred and maintained at reflux for 22 h (oil bath temp. 135-140° C.) under Ar. After cooling, the red solidified material was mixed with 120 mL of CHCl$_3$. Upon vigorous stirring and cooling with an external ice-bath, 10% aq. NaOH (36 mL) was added to the mixture at such a rate that the temperature did not exceed 0° C. The aqueous layer was separated and extracted with CHCl$_3$ (40 mL); organic solutions were combined and washed with brine (30 mL), saturated NaHCO$_3$ solution (40 mL), and dried over MgSO$_4$ under an argon atmosphere. Phenol 2-H (an air-sensitive compound, especially in solutions) was isolated by column chromatography on SiO$_2$ (50 g) using a three-component EtOAc/CH$_2$Cl$_2$/hexane (1:1:10) mixture as a mobile phase. The solvents were evaporated in vacuo at the temperatures not exceeding 35° C. to furnish 1.58 g (67%) of the compound 2-H, whose identity and purity was confirmed by the spectroscopic data given below; pale yellow crystals, m.p. 125-126° C. $^1$H NMR (300 MHz, CDCl$_3$): δ=1.29 (s, 6H), 1.92 (d, $^4J_{H,H}$=1, 3H), 1.93 (m, 2H), 2.61 (t, $^3J_{H,H}$=6.5 Hz, 2H), 3.24 (m, 2H), 4.70 (br. s, 1H, OH), 5.12 (q, $^4J_{H,H}$=1, 1H), 6.04 (d, $^3J_{H,H}$=8.3 Hz, 1H), 6.77 (d, $^3J_{H,H}$=8.3 Hz, 1H) ppm; $^{13}$C NMR (75.5 MHz, CDCl$_3$): δ 18.8 (Me), 21.2 (CH$_2$), 21.4 (CH$_2$), 26.7 (Me×2), 41.4 (CH$_2$), 55.9 (C), 102.4 (CH), 108.1 (C), 116.3 (C), 121.9 (CH), 126.9 (CH), 128.2 (C), 142.6 (C), 153.2 (C) ppm; EI-MS: m/z=229 (9) [M$^+$.], 214 (100) [M-Me]$^+$; MS (ESI): m/z (positive mode, %)=230 (48) [M+H]$^+$, 262 (100) [M+Na]$^+$; HRMS (C$_{15}$H$_{19}$NO): 230.15402 (found M+H), 230.15394 (calc.).

2,3,4,5-Tetrafluoro-6-(10-hydroxy-5,5,7-trimethyl-2,3-dihydro-1H,5H-pyrido[3,2,1-ij]quinoline-9-carbonyl)-benzoic acid (3)

Compound 2-H (1.57 g, 6.8 mmol) was refluxed with the tetrafluorophtalic anhydride (1.51 g, 6.9 mmol) in 22 mL of toluene for 5 h under an argon atmosphere. The precipitate was filtered, washed with hexane and dried in air. The crude product was dissolved in CHCl$_3$ (300 mL), the solution was stirred for 5 min with 1.5 g of SiO$_2$; a dark green material was removed by filtration, and the filtrate was diluted with 300 mL of warm (50° C.) hexane. The resulting solution was slowly evaporated to approx. ½ of its initial volume; the crystalline powder was filtered off and dried in air to furnish 2.19 g (71%) of the pure compound 3 as a bright yellow crystalline solid, which decomposed at about 280° C. $^1$H NMR (300 MHz, acetone-d$_6$): δ=1.37 (s, 6H), 1.71 (d, $^4J_{H,H}$=1.2, 3H), 1.87 (m, 2H), 2.61 (t, $^3J_{H,H}$=6.5 Hz, 2H), 3.24 (m, 2H), 5.27 (q, $^4J_{H,H}$=1.2, 1H), 6.75 (d, J=2 Hz, 1H), 12.7 (br.s, 1H) ppm; $^{13}$C NMR (75.5 MHz, acetone-d$_6$; highly splitted signals of the fluorinated $^{13}$C-atoms were not registered): δ 18.5 (Me), 21.0 (CH$_2$), 21.3 (CH$_2$), 28.6 (Me×2), 43.0 (CH$_2$), 58.6 (C), 106.1 (C), 109.9 (C), 115.4 (C), 125.5 (CH), 126.7 (C), 128.5 (CH), 149.9 (C), 162.7 (C), 163.1 (C), 188.7 (C) ppm; $^{19}$F NMR (282.4 MHz, acetone-d$_6$): δ=−155.1 (m, J=20, 4.5 and 1.5, 1 F), −152.0 (m, J=21, 7.2 and 3.4, 1 F), −141.5 (m, J=23, 12, 4.4 and 1.8, 1 F), −138.2 (m, J=21, 12 and 7.5, 1 F) ppm; HRMS (C$_{23}$H$_{19}$F$_4$NO$_4$): 448.1177 (found M−H), 448.1172 (calc.).

Rhodamine 4:

With some modifications, the recipe described in U.S. Pat. No. 6,372,907 was followed. In a typical experiment, a suspension of compound 3 (224 mg, 0.5 mmol) in 6 mL of 1,2-dichloroethane was stirred at RT with POCl$_3$ (0.19 ml, 2.0 mmol) for 15 min, then phenol 2-H (115 mg, 0.5 mmol) was added in one portion, and the stirring was continued at 63-65° C. (external oil bath) for 3.5 h under an argon atmosphere.

Upon cooling to RT, the dark blue solution was vigorously stirred for 1 h with 20 mL of water containing NaHCO$_3$ (505 mg, 6.0 mmol). The organic layer was separated, dried over Na$_2$SO$_4$, and the solvent was removed in vacuo. The chromatographic separation was performed over a column containing 70 g of SiO$_2$. The column was eluted with gradient CH$_2$Cl$_2$/CH$_3$CN (2/1→1/9), until brown and yellow impurities separated. Then the mobile phase was changed to CH$_2$Cl$_2$/MeOH (10:1→5:1); the main fraction, containing a blue dye with a red fluorescence, was collected and the solvents evaporated in vacuo to give 113 mg (35%) of rhodamine 4, whose identity and purity was confirmed by the spectroscopic data, TLC and HPLC. Bronze-like crystalline powder, insoluble in water, soluble in most organic solvents giving blue solutions with intense red fluorescence. HPLC: $t_R$=6.9 min (A/B 20/80-0/100 in 25 min, analytical column, detection at 616 nm). $^1$H NMR (300 MHz, CDCl$_3$): δ=1.42/1.43 (s, 12H), 1.86 (d, $^4J_{H,H}$=1.2, 6H), 1.99 (m, 4H), 2.90 (t, $^3J_{H,H}$=6.6 Hz, 4H), 3.47 (m, 4H), 5.37 (m, 2H), 6.88 (s, 2H) ppm; $^{13}$C NMR (75.5 MHz, CDCl$_3$; highly splitted signals of the fluorinated $^{13}$C-atoms were not registered): δ 18.7 (Me), 20.1 (CH$_2$), 20.7 (CH$_2$), 28.7/28.8 (Me×2), 43.1 (CH$_2$), 59.3 (C), 104.9 (CH), 113.8 (C), 121.2 (CH), 122.5 (C), 126.5 (C), 130.9 (C), 146.9 (C), 150.0 (C), 153.5 (C), 163.1 (C) ppm; $^{19}$F NMR (282.4 MHz, CDCl$_3$): δ=−159.0 (br. s, 1 F), −152.5 (t, J=22, 1 F), −140.1 (br. m, 1 F), −137.7 (dd, J=23 and 13, 1 F) ppm. MS (ESI): m/z (positive mode, %)=643 (100) [M+H]$^+$; HRMS (C$_{38}$H$_{34}$F$_4$N$_2$O$_3$): 643.2571 (found M+H), 643.2588 (calc.).

Compound 5-tBu:

Rhodamine 4 (224 mg, 0.35 mmol) and POCl$_3$ (0.27 ml, 2.80 mmol) was refluxed for 2.5 h in 12 mL of 1,2-dichloroethane under an argon atmosphere in a Schlenk flask. The solvent was removed in vacuo, the residue kept for an additional hour in vacuo (0.4-0.6 mbar) and, after argon had been introduced into the flask, dissolved in CH$_3$CN (10 mL). The flask was then cooled to −10° C. (external dry ice bath) and a solution containing N-methyl-β-alanine tert-butyl ester (free base, 64 mg, 0.40 mmol) and Et$_3$N (0.16 mL, 1.10 mmol) in 2 mL of CH$_3$CN was added in one portion upon stirring. After stirring for 15 min at RT, the solvent was removed in vacuo without heating, and the residue shaken with water (10 mL) and CH$_2$Cl$_2$ (40 mL). The organic layer was separated, washed with brine, dried over Na$_2$SO$_4$, and the solvent thoroughly removed in vacuo (0.1-0.2 mbar) to afford 260 mg (91%) of the title compound as an amorphous dark blue solid; insoluble in water, soluble in most organic solvents (except alkanes) with intense red fluorescence. HPLC: $t_R$=8.0 min (A/B 20/80-0/100 in 25 min, analytical column). $^1$H NMR (300 MHz, CDCl$_3$, 1:3 mixture of two amide rotamers with diastereotopic methyl and CH groups): δ=1.33/1.38 (s, 9H, tBuO), 1.48/1.51 (br. s, 12H), 1.80/1.82/1.86/1.88 (br. s, 6H, MeC═CH), 2.07 (br. m, 4H), 2.17/2.35 (m, 2H, CH$_2$CO), 2.86/2.87 (br. s, 3H, NMe), 2.98 (br.m, 4H), 3.45 (m, 2H, NCH$_2$), 3.58 (br. m, 4H), 5.46/5.48/5.49/5.54 (br. s, 2H), 6.44/6.56/6.61/6.70 (br. s, 2H) ppm; $^{19}$F NMR (282.4 MHz, 3.0 CDCl$_3$, 1:3 mixture of two amide rotamers): δ=−151.3/−150.4 (dt, J=22 and 4, 1 F), −148.7÷−149.0 (m, 1 F), −137.4/−136.9 (ddd, J=23, 12 and 5, 1 F), −135.2/−134.7 (ddd, J=23, 13 and 5, 1 F) ppm. MS (ESI): m/z (positive mode, %)=784 (100) [M$^+$]; HRMS (C$_{46}$H$_{50}$F$_4$N$_3$O$_4$$^+$*Cl$^-$): 784.3732 (found M$^+$), 784.3732 (calc.).

Compound 5-Me:

Rhodamine 4 (76 mg, 0.118 mmol) and POCl$_3$ (0.27 ml, 0.950 mmol) in 3 mL of 1,2-dichloroethane were heated at 60° C. for 3 h under an argon atmosphere in a Schlenk Flask equipped with a magnetic stirrer and a septum. The solvent was removed, the residue kept for an additional hour in vacuo (0.4-0.6 mbar) and, after argon had been introduced into the flask, dissolved in CH$_3$CN (4 mL). The flask was then cooled to 0° C., and a solution containing methyl 3-(N-methylamino) propionate hydrochloride (22 mg, 0.142 mmol) and Et$_3$N (0.050 ml, 0.360 mmol) in 1 mL of CH$_3$CN was added in one portion with stirring. After stirring for 15 min at RT, the solvent was removed in vacuo at 25° C., and the residue shaken with water (10 mL) and CH$_2$Cl$_2$ (20 mL). The organic layer was separated, washed with brine, dried over Na$_2$SO$_4$, and the solvent removed in vacuo. The crude compound was purified by flash-chromatography over SiO$_2$ (9 g) with a MeOH/CH$_2$Cl$_2$ (1:7) mixture as a mobile phase. Evaporation at RT and 0.4-0.6 mbar afforded 75 mg (81%) of the title compound. Amorphous dark blue solid, insoluble in water, soluble in most organic solvents (except alkanes) with intense red fluorescence. HPLC: $t_R$=10.4 min (A/B 80/20-10/90 in 25 min, analytical column). $^1$H NMR (300 MHz, CDCl$_3$, 1:3 mixture of two amide rotamers with diastereotopic methyl and CH groups): δ=1.48/1.51 (br. s, 12H), 1.78/1.81/1.85/1.87 (br. s, 6H, MeC═CH), 2.06 (br. m, 4H), 2.23 (m, 2H, CH$_2$CO), 2.78/2.85 (br. s, 3H, NMe), 2.99 (br.m, 4H), 3.47 (t, $^3J_{H,H}$=7, 2H, NCH$_2$), 3.59 (br. m, 4H), 5.46/5.47/5.51/5.54 (br. s, 2H), 6.43/6.51/6.61/6.69 (br.s, 2H) ppm; $^{19}$F NMR (282.4 MHz, CDCl$_3$, 1:3 mixture of two amide rotamers): δ=−151.0/−150.4 (dt, J=22 and 5, 1 F), −148.7 (m, 1 F), −137.3/−137.1 (ddd, J=23, 13 and 5, 1 F), −135.0/−134.7 (ddd, J=22, 12 and 5.5, 1 F) ppm. $^{13}$C NMR (75.5 MHz, CDCl$_3$; 1.3 mixture of two amide rotamers with diastereotopic methyl and CH groups; highly splitted signals of the fluorinated $^{13}$C-atoms were not registered): δ 18.5/18.6, 19.7/19.8, 20.6/20.7, 28.7/28.8, 31.2, 32.5/32.6, 37.20/37.23, 43.6/43.8, 51.7/52.0, 59.99/60.05, 105.7/106.5, 112.8, 114.0, 118.0, 120.8, 121.3, 122.8, 123.0, 124.8, 125.8, 132.2, 133.3, 150.3, 150.9, 153.2, 171.1/171.3 ppm; MS (ESI): m/z (positive mode, %)=742 (100) [M$^+$]; HRMS (C$_{43}$H$_{44}$F$_4$N$_3$O$_4$$^+$*Cl$^-$): 742.3255 (found M$^+$), 742.32625 (calc.).

Rhodamine 6:

tert-Butyl ester 5-tBu (32 mg, 0.04 mmol) was introduced in one portion into a vial containing 1.0 mL of the commercial (97%) sulfuric acid pre-cooled to 0° C. The vial was sealed, the mixture stirred at RT until the solid had completely dissolved, and left for 40 h. The viscous red solution was transferred to a vessel containing a frozen mixture (−10÷−15° C.; dry ice bath) of 1,4-dioxane (2 mL) and dry diethyl ether (5 mL). Then a larger amount of diethyl ether (40 mL) was added followed by hexane (15 mL). After standing at 0° C. for 1 h, the liquid was decanted from a blue viscous oil which was then thoroughly washed with absolute diethyl ether (4☐10 mL). The crude product was dissolved in 5 mL of water and subjected to chromatography over a column with Polygoprep 60-50 C18 (30 g). The column was eluted with water (50 mL) to remove the residual sulfuric acid, then with CH$_3$CN/H$_2$O (1:2) containing 0.05% (v/v) CF$_3$COOH. The first (main) fraction was collected, and the bulk of the solvent evaporated in vacuo. Subsequent freeze-drying furnished 26 mg (72%) of the title compound, whose purity (HPLC-area 99%) and identity (structure 6) was confirmed by the spectroscopic methods. Upon prolonged storage or moderate heating in methanol-containing solutions, particularly in the course of solvent evaporation, compound 6 formed the corresponding methyl ester (6-Me; the structure is given below), whose MS and HRMS (ESI) agreed with the proposed structure. Dark blue crystalline powder, soluble in water and polar organic solvents (with an intense red fluorescence), insoluble in diethyl ether, aliphatic, chlorinated, and aromatic hydrocarbons. HPLC: $t_R$=13.0 min (100%, A/B 80/20-50/50 in 25 min, analytical column), RP TLC: $CH_3CN/H_2O$ (1:1)+0.1% $CF_3COOH$ (v/v), $R_f$~0.2. $^1H$ NMR (300 MHz, $D_2O$): δ=1.63/1.65/1.69/1.71 (br. s, 12H), 1.91/1.93 (s, 6H, MeC═CH), 2.02 (br. m, 4H), 2.55 (m, 2H, $CH_2CO$), 2.83/2.90 (br. s, 3H, NMe), 2.98 (br. m, 4H), ~3.5 (br. m, 2H, $NCH_2$), ~3.7 (br. m, 4H), 3.94 (d, $^2J_{H,H}$=13, 2H, $CH_AH_B$), 4.32 (d, $^2J_{H,H}$=14, 2H, $CH_AH_B$), 6.14/6.16 (br. s, 2H), 7.32 (br.s, 2H) ppm; $^{19}F$ NMR (282.4 MHz, $D_2O$; ca. 1:9 mixture of the two amide rotamers; signals of the major rotamer are given): δ=−150.8 (dt, J=21 and 5.5, 1 F), −149.3 (dt, J=22 and 5.5, 1 F), −138.7 (ddd, J=22, 11 and 5.5, 1 F), −136.0 (m, 1 F) ppm. $^{13}C$ NMR (75.5 MHz, $D_2O$; highly splitted signals of the fluorinated $^{13}C$-atoms were not registered): δ 16.7/16.8 ($CH_2$), 17.4 ($CH_2$), 24.6/24.87/24.93/25.1 (Me; disappear in compound 6D), 28.3 ($CH_2$), 35.9 (NMe), 40.9/41.0/41.1 ($CH_2$), 50.5/50.9 ($CH_2SO_3$; disappear in compound 6D), 57.4/57.7 (C), 104.0/104.3 (C), 109.7/110.3 (C), 117.6 (C), 118.1 (CH), 119.4 (C), 119.9 (CH), 135.5/136.2 (CH═[CMe]; disappear in compound 6D), 137.9 (C), 147.8/148.3 (C), 150.1/150.2 (C), 160.2 (C), 171.8 (CO) ppm; MS (ESI): m/z (negative mode, %)=442.6 (100) [M−2H]$^−$, 908 (45) [M−2H+Na]$^−$; m/z (positive mode, %)=910 (49) [M+Na]$^+$, 932 (45) [M−H+2Na]$^−$; HRMS ($C_{42}H_{41}F_4N_3O_{10}S_2$): 888.22386 (found M+H), 888.22423 (calc.); 910.20587 (found M+Na), 910.20617 (calc.).

Methyl Ester 6-Me.

MS ESI): m/z (positive mode, %)=902 (100) [M+H]$^+$, 924 (27%) [M+Na]$^+$; (ESI): m/z (negative mode, %)=900 (100) [M−H]$^−$; HRMS ($C_{43}H_{43}F_4N_3O_{10}S_2$): 902.23994 (found M+H), 902.23988 (calc.).

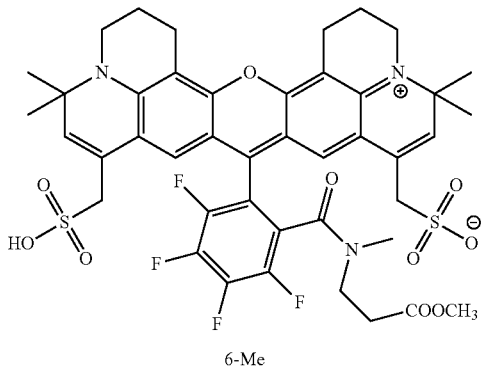 [SMILES: COC(=O)CCN(C)C(=O)c1c(F)c(F)c(F)c(F)c1C1=c2cc3c4c(c2Oc2c1cc1c5c2CCCN5C(C)(C)C=C1CS(=O)(=O)O)CCC[N+]=4C(C)(C)C=C3CS(=O)(=O)[O-]]

6-Me

Rhodamine 5-H:

Compound 5-tBu (30 mg, 0.038 mmol) was dissolved in dry dioxane (1 mL) and 4 M HCl solution in dry 1,4-dioxane (1 mL) was added at 0° C., and then the reaction mixture was left for 2 days at RT. The solution was mixed with $CH_2Cl_2$ (40 mL), washed with brine (2×10 mL), dried and evaporated to dryness in vacuo. The pure title compound was isolated in 70% yield by flash chromatography over 15 g of $SiO_2$ with $CH_3CN/H_2O$ (1:10→1:3) mixture as a mobile phase. Dark blue crystalline powder, very slightly soluble in water, moderately soluble in polar organic solvents, also in $CHCl_3$ and $CH_2Cl_2$. HPLC: $t_R$=5.0 min (100%, A/B 20/80-0/100 in 25 min, analytical column). $^1H$ NMR (300 MHz, $CDCl_3$, ca. 1:1 mixture of two amide rotamers with diastereotopic methyl and CH groups): δ=1.45/1.49 (br. s, 12H), 1.88/1.90 (br. s, 6H, MeC═CH), 2.05 (br. m, 4H), 2.35 (br. m, 4H, $CH_2CO$), 2.74/2.79 (br. s, 3H, NMe), 2.95 (br. m, 4H), 3.15 (m, 2H, $NCH_2$), 3.54 (br. m, 4H), 5.43/5.44/5.49/5.50 (br. s, 2H), 6.43/6.62/6.69/6.74 (br. s, 2H) ppm; $^{19}F$ NMR (282.4 MHz, $CDCl_3$, 1:1 mixture of two amide rotamers): δ=−152.2 (m, 1 F), −149.4/−148.4 (m, 1F), −134.5 (m, 2 F) ppm. MS (ESI): m/z (positive mode, %)=728 (100) [M$^+$] 750 (60) [M+Na]$^+$; HRMS ($C_{42}H_{41}F_4N_3O_4$): 728.3100 (found M+H), 728.3106 (calc.); 750.2923 (found M+Na), 728.2925 (calc.).

Saponification of the Ester 5-Me (an Alternative Procedure for the Preparation of the Acid 5-H).

A freshly prepared aqueous 10 wt. % KOH solution (0.045 mL, 0.080 mmol) was diluted with water (1.5 mL) and combined with a solution of methyl ester 5-Me (14 mg, 0.018 mmol) in THF (1.2 mL) at RT. The resulting homogeneous solution was left overnight in a sealed vial, then acidified with 1 M aq. HCl (0.3 mL, 0.3 mmol), mixed with brine (10 mL) and extracted with $CH_2Cl_2$ (2☐30 mL). The extract was washed with brine (10 mL), dried over $Na_2SO_4$ and evaporated in vacuo to afford 10 mg (68%) of a pure (~99%, HPLC) product, which proved to be identical (spectroscopic data, HPLC retention parameters) to the previously obtained acid 5-H; no additional purification required.

Sulfonation of the Acid 5-H.

Rhodamine 5-H was sulfonated with $H_2SO_4$ under conditions described above for the tert-butyl ester 5-tBu and gave the product identical to the previously obtained rhodamine 6 (HPLC, spectroscopic data) in an 88% yield.

N-hydroxysuccinimidyl Ester 9:

To rhodamine 6 (5-10 mg, 6-12 μmol), taken as a 2% solution in dry DMF, $Et_3N$ (60-12 μmol) was added followed by TSTU (24-48 μmol), which was added at RT in small portions over a period of 5-15 h, while the reaction was monitored by HPLC (A/B: 80/20, 50/50 in 25 min, 1 mL/min, detection at 636 nm, analytical column) The solvent was removed in vacuo (<1 mbar) at the temperatures not exceeding 30° C., and the ester 9 isolated by means of preparative HPLC: $t_R$=16.0 min (A/B 20/80-0/100 in 25 min, preparative column) followed by freeze drying of the fractions. Dark blue solid soluble in water (purity check gave 98% HPLC area); decomposes in aqueous solutions at RT, stable in a solid state under Ar at −20° C. MS (ESI): m/z (negative mode, %)=983 (100) [M−H]$^−$; HRMS ($C_{46}H_{44}F_4N_4O_{12}S_2$): 983.2400 (found M−H), 983.2261 (calc.).

Maleimide 11 was synthesized from the freshly prepared NHS ester 9 (2 mg, 2.2 μmol) and N-(2-aminoethyl)maleimide trifluoroacetate (2.8 mg, 11 μmol) which were combined in dry DMF (0.2 mL) in the presence of $Et_3N$ (3 μl, 21 μmol) at room temperature and left with stirring overnight. The solvent was evaporated in vacuo (1 mbar), and the title compound was isolated by preparative HPLC; $t_R$=15.4 min (A/B 20/80-50/50 in 25 min, analytical column, 636 nm) followed by freeze drying of the fractions. Dark blue solid soluble in water (purity check gave 100% HPLC area); MS (ESI): m/z (negative mode, %)=1008 (100) [M−H]$^−$. It decomposes in methanol containing solutions (adding one molecule of MeOH, apparently with opening of the maleimide cycle and forming the compound with M=1041; [M−H]=1040 in the negative mode of the electro-spray ionization); stable in a solid state under Ar. The title compound reacts with N-acetylcysteine in aq. $NaHCO_3$ at pH=7.5 forming the conjugate with $t_R$=13.8 min (A/B 20/80-50/50 in 25 min, analytical column, 636 nm).

2,3,5,6-Tetrafluorophenyl Ester 8:

Rhodamine 7 (6 mg, 7 μmol) in 2.5 mL of dry $CH_3CN$ was mixed with 2,3,5,6-tetrafluorophenol (1.68 mg, 10 μmol, 1% solutions in $CH_2Cl_2$), and the commercial $Me_2NCH_2CH_2N$═C═NEt (free base, 1.37 mg, μmol, 1% solutions in $CH_2Cl_2$ was added over a period of 2 h. The reaction was monitored by TLC on $SiO_2$ with $CH_3CN/H_2O$ (1:10) mixture as a mobile phase. Compound 8 was isolated in 65% yield using HPTLC plates (normal phase $SiO_2$) with the same eluent followed by freeze drying. HPLC: $t_R$=18.0 min (70-80% HPLC area, A/B 20/80-0/100 in 25 min, analytical column). For the preparative experiments, the active ester 8 was used without further purification. MS (ESI): m/z (positive mode, %)=876 [M⁺]; HRMS ($C_{48}H_{42}F_8N_3O_4^+$*OH⁻): 876.3052 (found M⁺), 876.3042 (calc.).

Example 2

Synthesis of Deuterated Rhodamine Compounds

Deuterated Analogue of Compound 1.

The method for the preparation of 1 outlined by L. A. Robinson and M. E. Theoclitou [*Tetrahedron Lett.* 2002, 43, 3907-3910] was used utilizing $[D_6]$-acetone as a starting material. An additional treatment of the evaporated reaction mixture with MeOD in order to "restore" the methine deuterium atoms in the fragment $CCD_3=CD$ was necessary. They proved to be largely (and unexpectedly) exchanged to H in the course of the synthesis. Presumably, the methine groups coordinate to the ytterbium catalyst and then receive protons from $H_2O$ formed in the course of the reaction or added during the work-up.

Finely powdered ytterbium(III) triflate (the commercially available hydrate, 1.30 g, ~26 mmol) was dried in a Schlenk flask with stirring at 130° C. for 1.5 h. Then the flask was filled up with argon, cooled to 0° C., and a solution of m-anisidine (1.75 g, 14 mmol) in $[D_6]$-acetone (92 mL, 1.14 mol) was added in one portion through a septum. The mixture was stirred overnight at RT, the solvent removed in vacuo at 25-30° C., MeOD (10 mL) was added to the residue followed by $CH_2Cl_2$ (200 mL), and it was well shaken with water (30 mL). The organic layer was separated, washed with brine (30 mL), dried over $Na_2SO_4$ and evaporated in vacuo. Column chromatography on $SiO_2$ (90 g) with $CH_2Cl_2$/hexane mixture (1:3.1:1) as an eluent furnished the deuterated compound 1 (1.76 g, 59%). The intensity of the singlet signal at 5.2 ppm (CH group at the double bond) in the $^1H$ NMR spectrum ($CDCl_3$) indicated the degree of deuteration of ca. 50% at this carbon atom, while other aliphatic protons, which originated from acetone-$[D_6]$, were deuterated to a degree of about 90% and more. To further improve the deuterium content, the obtained product (1.76 g, 0.83 mmol) was heated with a reflux condenser at 50° C. in 25 mL of $CH_3OD$ (0.72 mol) with 96% $D_2SO_4$ (0.87 g, 15 mmol) for 30 h. The solution was cooled to −35° C. (dry ice bath), neutralized with an excess of dry $Na_2CO_3$ (1.40 g, 13 mol) upon stirring, and evaporated in vacuo at RT. The residue was extracted with $CH_2Cl_2$, evaporated and subjected to column chromatography exactly as described above (using 50 g of $SiO_2$), which afforded 1.23 g (41%) of the deuterated compound 1 with the higher degree of deuteration (ca. 75%).

Compound 6D was obtained from the deuterated analogue of compound 1 as described above using $Na_2CO_3$ (instead of $NaHCO_3$) and $CD_3CN$ in the alkylation step, followed by treatment with 48% DBr in $D_2O$ (Deutero GmbH) in AcOD for the dealkylation. Further steps of the synthesis were performed exactly as described for the non-deuterated compounds (see above). The sulfonation of the deuterated compound 5-tBu (65 mg, 0.08 mmol) was performed with 96% $D_2SO_4$ in $D_2O$ (VWR International). It improved the deuterium content in the fragment $C(CD_3)=CD$ of the title compound. Yield—30 mg (41%). MS (ESI): m/z (negative mode, %)=451.7 (100) [M−2H]⁻, 904.4 (45) [M−H]⁻; $C_{42}H_{23}D_{18}F_4N_3O_{10}S_2$: 905.4. Molecular mass distribution of the molecular ion peaks was as follows: m/z (negative mode, %)=900 (15), 901 (36), 902 (67), 903 (94), 904 (100), 905 (46%), 906 (18%). Subtracting the natural deuterium content, this molecular mass distribution corresponds to the following amounts of the new deuterium atoms, introduced in the course of the labelling procedures: 905 ($D_{18}$): 5%; 904 ($D_{17}$): 43%; 903 ($D_{16}$): 24%; 902 ($D_{15}$): 13%; 901 ($D_{14}$): 8%.

NHS Ester 9D was prepared from acid 6D (11 mg, 12 µmol) and N-hydroxysuccinimide (13 mg, 0.11 mmol) dissolved in dry DMF (0.5 mL). HATU (12 mg, 32 µmol) was added to this solution at room temperature followed by $Et_3N$ (25 µl, 0.17 mmol), and the reaction mixture was stirred under Ar overnight. The solvent was removed in vacuo, and the title compound was isolated by preparative HPLC. Dark blue very light powder; HPLC: $t_R$=15.6 min (A/B 20/80-0/100 in 25 min, analytical column). MS (ESI): m/z (negative mode, %)=1001.4 (100) [M−H]⁻; $C_{46}H_{26}D_{18}F_4N_4O_{12}S_2$: 1002.4. Molecular mass distribution of the molecular ion peaks was as follows: m/z (negative mode, %)=997 (16), 998 (37), 999 (70), 1000 (97), 1001 (100), 1002 (54), 1003 (21).

Example 3

Microinjection Tests of Compound 6 and of the Commercial Dye Atto 647N

The commercial dye Atto 647N is preferred in many fluorescence microscopy studies, especially when high excitation powers are used. It has a superior photo stability compared to other dyes. For live cell studies, it is desirable to introduce aqueous solutions of the dye (e.g. coupled to antibodies) via microinjection into cells. However, it was found that this is impossible with the Atto 647N dye because it is too lipophilic and sticks to the walls of the glass capillaries used for injection. These tests were performed with a ~0.5 µM solution of Atto 647N in water or PBS, filled into microinjection pipettes (Femtotips®, Eppendorf, Hamburg, Germany and home made capillaries). The capillaries got blocked by the dye and no fluid could be injected, even under the maximally available pressure of ~4000 hPa. The walls, but not the interior of the capillaries brighten up when irradiated. On the other hand, if 50% (v/v) ethanol is used as solvent, a 0.5 µM solution is injectable, but this solvent system is not compatible with live cells.

Thereafter, the suitability of the dye 6 for microinjection was tested under the same conditions: A 0.5 µM solution of the dye in water was filled into the capillary tubes (Femtotips®). Neither the walls of the capillaries lit up noticeably upon fluorescence excitation, nor were the capillaries blocked: upon application of a normal injection pressure (~90 hPa), the flow was not impeded. Aqueous solutions of dye 6 thus proved suitable for microinjection.

Example 4

Stimulated Emission Depletion Studies

The bleaching resistance of rhodamine 6 and the commercial dye Atto647N were compared in (fixed) biological samples. Both dyes (as NHS esters) were coupled to goat-anti-rabbit antibodies (Dianova, Hamburg, Germany), and these were used for staining the mitochondrial protein Tom20 in mammalian cells (cell line U2OS). A Tom20 specific antibody (from rabbit) (Santa Cruz Biotechnology, Heidelberg, Germany) was used as a primary label. From 50 up to 100 frames were imaged from the same region. The bleaching stability was determined by exponential fits to the fluorescence intensity in selected regions of interest. It was found that the bleaching stability of compound 6 under excitation by light of 635 nm followed by depletion at 750 nm (used in STED microscopy) is comparable with the commercial dye Atto 647N. However, excitation with 635 nm light alone (without depletion at 750 nm) revealed that under these conditions the photostability of dye 6 is ca. 8 times lower than that of the Atto 647N.

The bleaching resistances of the compounds 6 and 6D were compared in fixed human cells (cell line U373). The NHS esters of both dyes were coupled to sheep-anti-mouse antibodies (Dianova, Hamburg, Germany) and used to stain β-tubulin via anti-β-tubulin antibodies from mouse (Sigma, Munich, Germany). Up to 100 frames were imaged from the same region and the bleaching stability was determined by exponential fits to the fluorescence intensity in selected regions of interest. Under excitation with 635 nm light and under STED imaging conditions (pulsed excitation with 635 nm and pulsed depletion at 750 nm, overlaid Gaussian foci), we found the bleaching resistance to vary stronger between samples than between the undeuterated and deuterated substances (6 and 6D).

Figure 2:
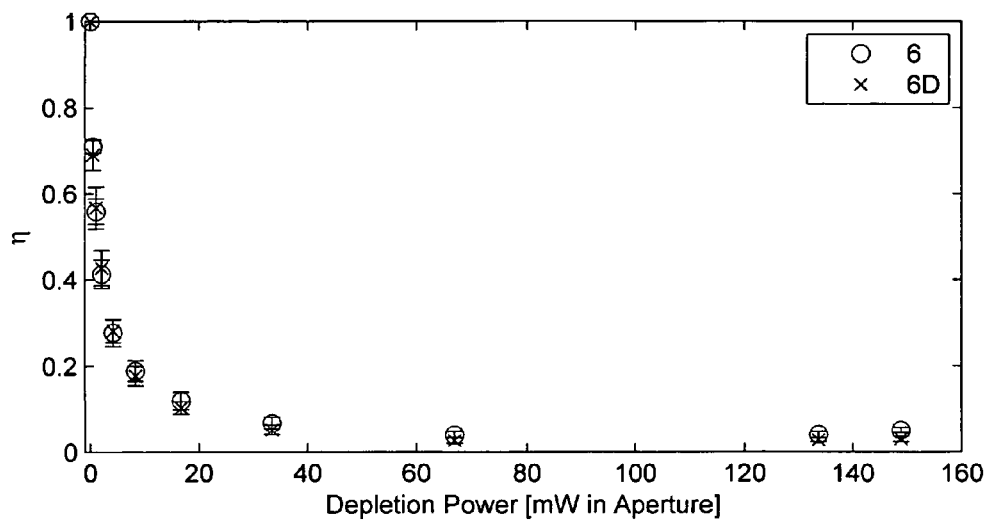
FIG. 2. Decrease in the fluorescence intensity η as a function of the (time averaged) depletion beam power. Compounds 6 and 6D behave very similarly.

The depletion of the fluorescence as a function of the depletion beam intensity was measured for the dyes 6 and 6D in the same samples of U373 cells (FIG. 2). Excitation power was 2.7 μW. No differences in the depletion efficiency ("STED efficiency") were detected within the measuring accuracy.

Example 5

Conjugation with Antibodies and Immunolabelling Experiments

It was found that the hydrophilic dyes 6/6D do not integrate into biological membranes. With respect to biological labelling, this is the most important advantage of these dyes over the lipophilic fluorescent stains with similar spectral properties (e.g. Atto 647N).

The water-soluble compounds 6/6D can be used in a variety of mounting media: e.g. aqueous solutions, glycerol-based media like Mowiol [6 g glycerol, 2.4 Mowiol 4-88 (Hoechst), 6 mL $H_2O$, 12 mL of 0.2 M Tris buffer (pH 7.2) and 2.5 wt. % 1,4-diazabicyclo[2.2.2]octane], TDE embedding medium [97% of 2,2'-thiodiethanol and 3% of phosphate buffer], and others.

Due to the presence of various reactive groups (e.g. NHS-ester and maleimide), fluorescent dyes 6/6D may be conjugated with various reactive sites in primary or secondary antibodies, proteins, toxins, carbohydrates, lipids or any other compounds. The unpolar and lipophilic dye 5-H may be used in the form of its active ester 8 for labelling of unpolar compounds (e.g. lipids in their unpolar domains). Once the polar hydrophilic dyes 6/6D do not integrate into biological membranes, they may be used at high concentrations in labelling experiments. Two- and multi-colour experiments with other dyes are also possible (e.g. for colocalization of various biological objects).

The degree of labelling achieved with antibodies may strongly vary; typically, compounds 6/6D (taken as their NHS esters 9/9D) attached to the anti-rabbit and anti-mouse antibodies produced a labelling degree from 2.5 up to 6. The fluorescence quantum yields of the conjugates were found to be 48% (for the dye 6 and sheep anti-mouse antibodies) and 40% (for the dye 6 and goat anti-rabbit antibodies). Decrease in fluorescence quantum yields after conjugation with antibodies is normal and well documented [cf.: V. P. Boyarskiy, V. N. Below, R. Medda, B. Hein, M. Bossi, S. W. Hell, *Chem. Eur. J.* 2008, 14, 1784-1792].

Figure 3:
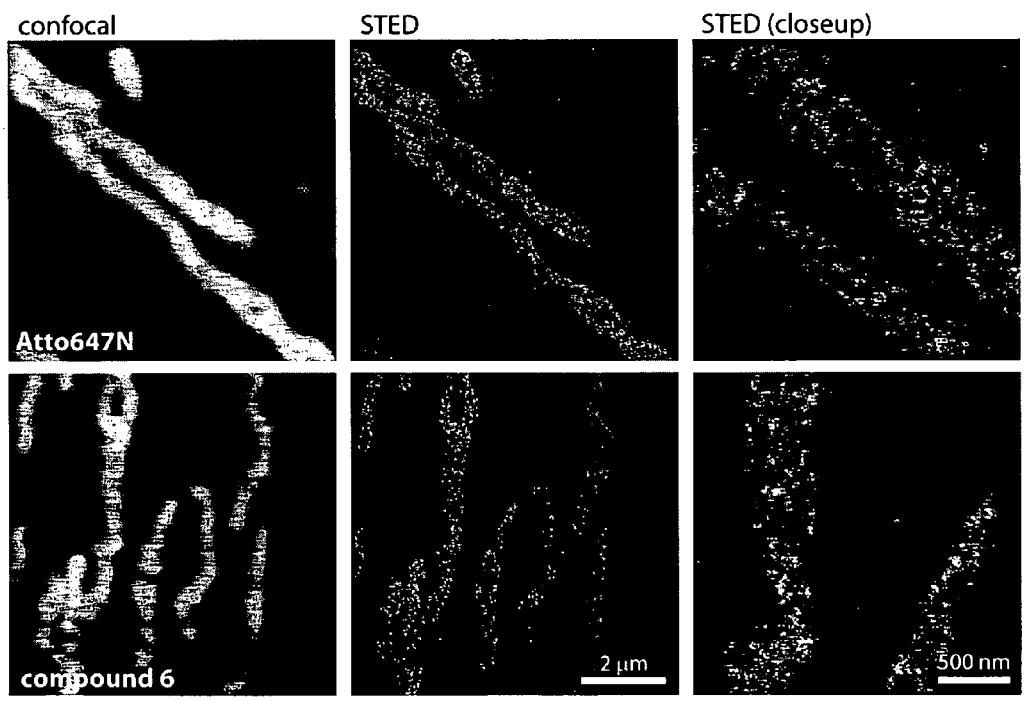
FIG. 3. PtK2 cells with stained mitochondria. The rhodamine derivative 6 has been used in the form of the NHS ester for the labelling of the (secondary) anti-rabbit antibodies.

To evaluate the performance of the new dyes in optical microscopy, the mitochondrial entry gate—the TOM complex—was stained in formaldehyde-fixed Ptk2 cells with a Tom20 specific primary antibody (Santa Cruz Biotechnology, Santa Cruz, Calif., USA). A fluorescent antibody labelled with the compound 6 was applied as a secondary marker (FIG. 3, lower panels). For comparison, the same secondary antibodies were labelled with Atto 647N fluorophore and used for imaging of the TOM complex (FIG. 3, upper panels). Imaging was performed with the STED microscope described recently [B. Harke, J. Keller, C. K. Ullal, V. Westphal, A. Schönle, S. W. Hell, *Opt. Expr.* 2008, 16, 4154-4162]. The confocal and STED images obtained with the new fluorescent dye 6 demonstrate a low cellular and mitochondrial background caused by unspecific binding. In the STED images with the new dye, an effective point spread function with a full width at half maximum below 40 nm was observed in small structures, demonstrating the applicability of dye 6 for high resolution imaging.

Example 6

Fluorescent Dyes 6 and 6D as Molecular Mass Distribution Tags

Figure 4:
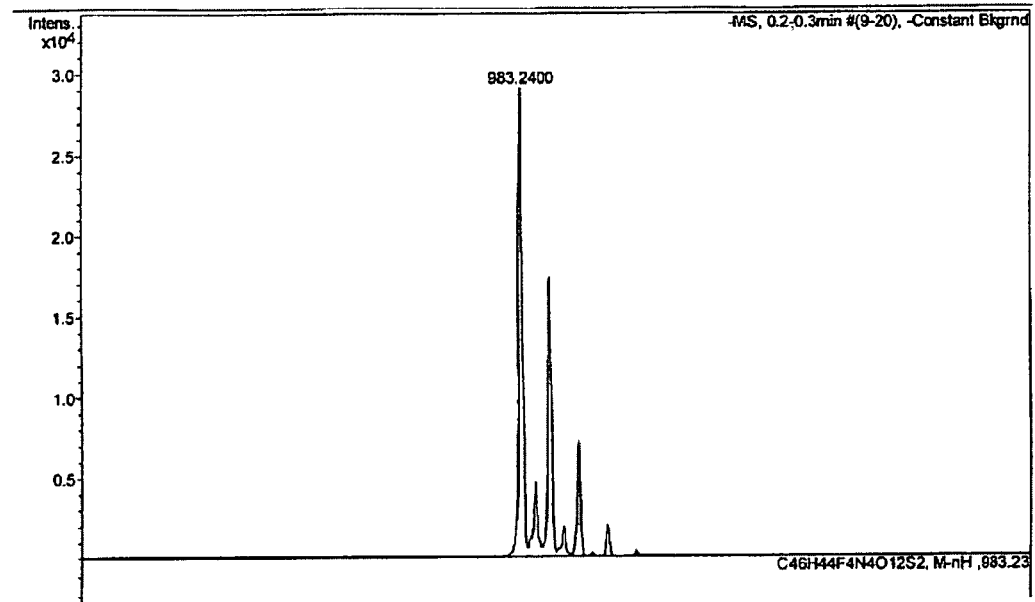
FIG. 4. Electro spray ionization spectra (negative mode) of the NHS esters 9 (upper panel) and 9D (lower panel) displaying the natural and artificial molecular mass distributions of the molecular ions, respectively.

The hydrophilic fluorescent dye 6 ($C_{42}H_{41}F_4N_3O_{10}S_2$, M=887) with up to 18 hydrogen atoms replaced with deuterium at certain aliphatic groups was prepared (Scheme 1 and 2). As a result, in the negative mode of the ESI mass-spectrum the highest peak with m/z=904 (M−H) corresponded to the molecular formula $C_{42}H_{23}D_{18}F_4N_3O_{10}S_2$ (M=905). The presence of 18 deuterium atoms indicates the maximally possible degree of substitution achieved using deuterated acetone as a precursor. However, peaks corresponding to lower masses are also present. Molecular mass distribution of the molecular ion peaks in compound 6D was the following: m/z [negative mode] (relative intensity, %)=900 (15), 901 (36), 902 (67), 903 (94), 904 (100), 905 (46%), 906 (18%). After subtraction of the natural deuterium content, this molecular mass distribution corresponds to the following amounts of the new deuterium atoms, introduced in the course of the labelling procedures: 901 ($D_{14}$): 8%; 902 ($D_{15}$): 13%; 903 ($D_{16}$): 24%; 904 ($D_{17}$): 43%; 905 ($D_{18}$): 5%. FIG. 4 shows the electro spray ionization spectra (negative mode) of the NHS esters 9 (upper panel) and 9D (lower panel) displaying the natural and artificial molecular mass distributions of the molecular ions, respectively. Molecular mass distribution patterns in compounds 6D and 9D were found to be identical, so that no stable isotope "leaking" was observed in the course of chemical transformations. Similar molecular mass distribution patterns could easily be found in the positive mode of the ESI mass spectra of the sulfonated rhodamines 6D and 9D, too. However, in this mode these spectra are complicated by clustering with sodium and other positively charged ions.

Compounds 6D and 9D have the same narrow molecular mass distribution patterns, so that all their derivatives could easily be recognized and identified by their mass spectra. The characteristic feature is the symmetry of the molecular ion peaks due to the presence of the ions with lower molecular masses. Moreover, selective derivatization of the amines (with compound 9D) or thiols (with the deuterated analogue of the maleimide 11) makes the group identification of the biologically important substance classes possible simply by comparison of the ESI mass spectra of the native sample before and after the reaction with the pairs of the reagents 9 and 9D or 11 and its deuterated analogue. Importantly, the deuterated reagents (e.g. 9D) produce not only a new molecular mass distribution pattern in the derivatives, but also a considerable isotopic shift of 17-18 Da. Consequently, new peaks do not overlap with the peaks of the derivatives obtained from compounds 9 or 11. Therefore, it may even be advantageous, if the substances 9 and 9D (or 11 and its deuterated counterpart) are used as mixtures for derivatization of proteins, tryptic peptides and other complex biological samples. For very complex mixtures, HPLC separation prior to the mass-spectroscopic analysis may be used. It was shown that under reversed-phase HPLC conditions compounds 6 and 6D, as well as 9 and 9D, are inseparable and have the same retention times. Thus, their derivatives are also expected to give the same peaks under HPLC conditions. An important issue is the lower peak intensity of the molecular ions of the deuterated substances (e.g. 6D and 9D) compared with the undeuterated analogues (6 and 9) taken in the same concentrations. Thus, a relative content of a deuterated compound in a reagent mixture with an unlabelled counterpart has to be 3-4 times higher, so that the intensities of the two peaks in the mass spectrum of the derivatized analyte will be comparable and easy to find. New molecular mass distribution tags introduced here are coloured and highly fluorescent. These properties are indispensable for analytical purposes, because fluorescence and mass spectroscopy detection limits are similar (picograms of an analyte can easily be detected).

Example 7

Bleaching Measurements

Figure 5:
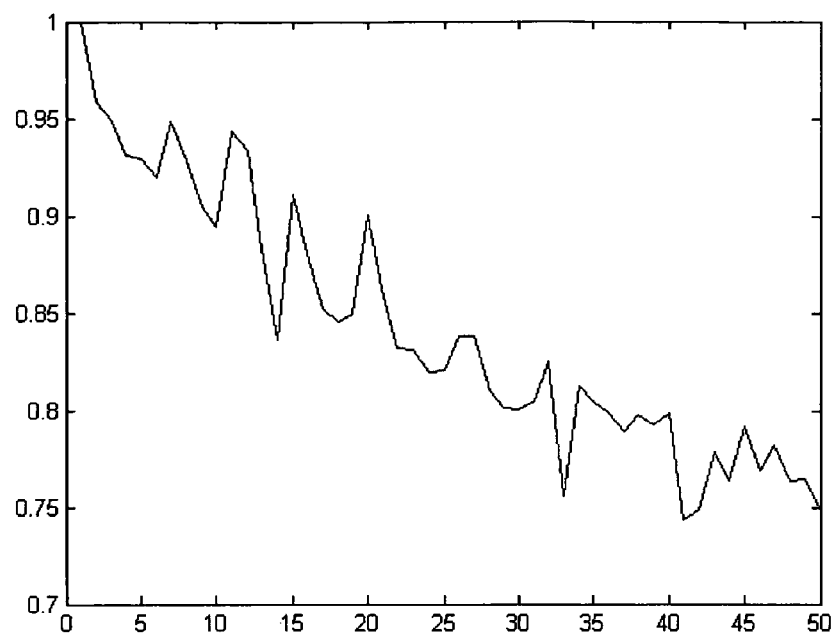
FIG. 5. Decrease in the fluorescence intensity of an aqueous solution of compound 6 by photodecomposition.

The degree of photodecomposition was evaluated by measuring the decrease in the fluorescence intensity of compound 6 (FIG. 5). The x-axis in FIG. 5 displays the number of pump-probe cycles and the y-axis—the brightness relatively to that after the first pulse. The pulse duration was 10 ms, and the pulse power 18.3 kW/cm$^2$ (633 nm CW laser light). Photostability of compound 6 is strong: 50 pump-probe cycles with a pump intensity of 18 kW/cm$^2$ only bleach 25% of the ensemble allowing for a high number of single-molecule returns, i.e. a high number of single-molecule localizations and thus a final image with high contrast. Thus, the degree of photo-bleaching was found to be low, taking into consideration the very strong light intensities and the presence of air-oxygen.

Example 8

Ground State Depletion Studies of Compound 6

Figure 6:
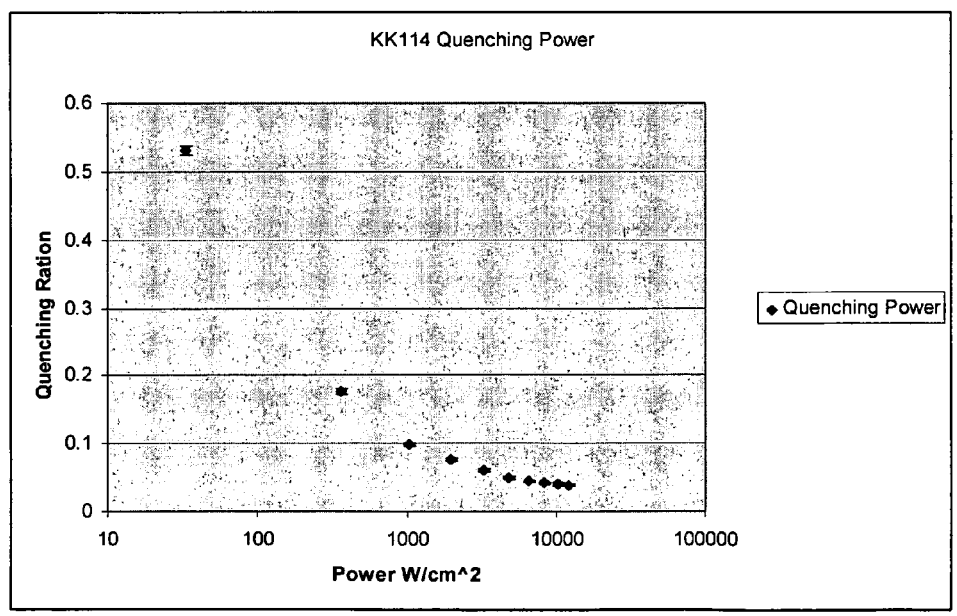
FIG. 6. Evaluation of the laser power by ground state depletion of compound 6 by the pump-probe experiment with 633 nm pulsed light.
Figure 7:
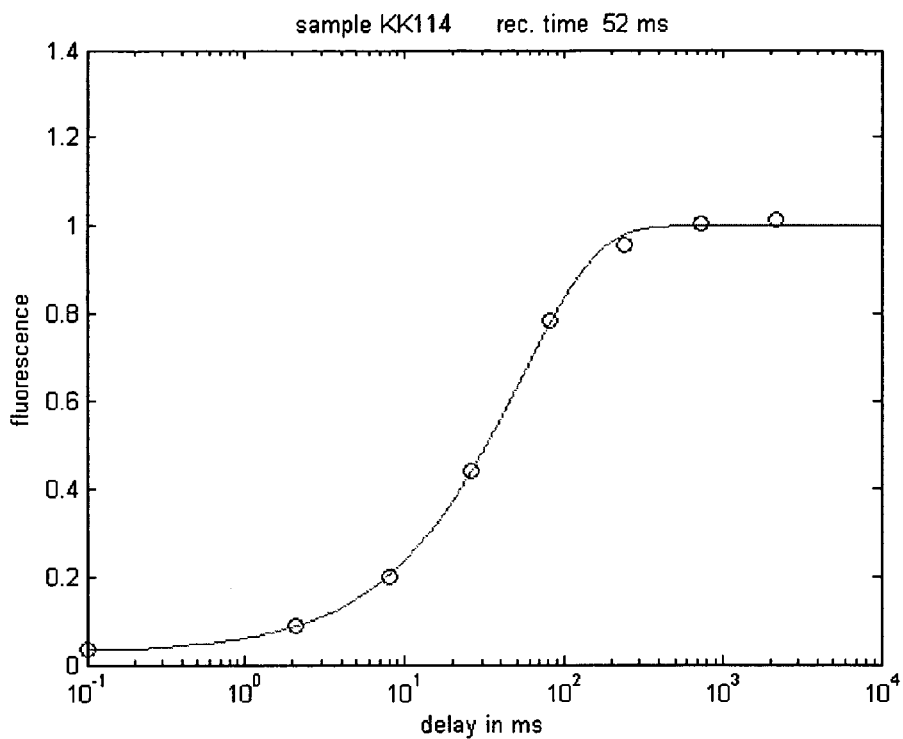
FIG. 7. Recovery kinetics of the dye 6 undergoing the transition to the fluorescent ground state ($S_0$) from the dark state.
Figure 8:
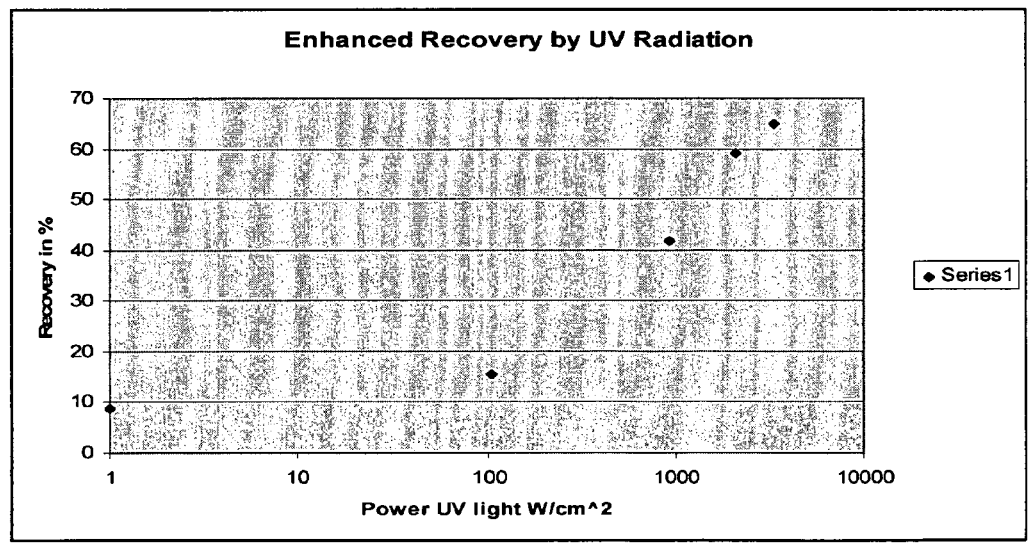
FIG. 8 Enhanced recovery of the compound 6 from the dark state by irradiation with the UV laser (375 nm).

The compound 6 is excellent for super-resolution far-field microscopy based on ground-state depletion, such as GSDIM (ground-state depletion followed by individual molecule return; J. Fölling et. al, *Nature Meth.* 2008, 5, 943-945). Here, "off" and "on" switching of the fluorescence is achieved by transiently shelving the fluorophore into a metastable dark state. Upon the return of only a few isolated single molecules to the fluorescent singlet state, positions of these single light emitting spots can be imaged on a camera and localized with high precision. Upon repeating this procedure and acquiring many pictures, a super-resolution image can be reconstructed from the localized positions. A prerequisite of this method is that >90% of the ensemble of the applied fluorescent dye can be shelved into a dark state at a time (to ensure the detection of isolated fluorescent spots at a time in a densely labeled sample) and that the fluorophore is bright enough, i.e., that it emits enough photons while being in the singlet on-state (to ensure high precision of localization). FIG. 6 shows that at laser intensities I>10 kW/cm$^2$ of continuous-wave (CW) 633 nm laser light 97% of all fluorophores of compound 6 in poly(vinyl alcohol) matrix can be switched-off at a time. Switching off of the laser leads to a recovery of the fluorescence ensemble within a characteristic recovery time of 50 ms (FIG. 7), indicating the shelving into a metastable dark state. The measurements of FIGS. 6 and 7 were performed in a pump-probe mode, i.e., the residual level of fluorescence was probed with I=100 W/cm$^2$ for 0.5 ms after strong irradiation for 10 ms with the given laser intensity. Further on, recovery of the fluorescence can be accelerated by addition of UV light, which leads to an optically-induced de-population of the dark states. Already 2 kW/cm$^2$ of 375 nm light recovers 60% of the fluorescence within an irradiation period of 1 ms (FIG. 8). This is important in cases of samples of low label density where the addition of UV light and thus acceleration of dark state return helps to accelerate image acquisition.

Summarizing, the present invention provides new and improved photostable rhodamine dyes of the general structural formulae I, ID, II, and IID which may be used as efficient fluorescent markers. They may readily be excited with 633/635 nm laser light, perform very well in conventional and stimulated emission depletion (STED) microscopy and fluorescence correlation spectroscopy, especially with very high light intensities. The new fluorescent dyes emit light at about 660 nm, possess high values of the fluorescence quantum yields in solution (up to 80%), relatively long excited state lifetimes (>3 ns) and are resistant against photobleaching under STED conditions (with depletion at 750 nm) in the presence of air-oxygen. The new fluorescent dyes possess relatively low rates of the intersystem crossing. Starting from the same chromophore-containing scaffold (I), both lipophilic (e.g. 5-H) and hydrophilic (e.g. 6) derivatives are easily available. After attaching amino or thiol reactive sites, the modified derivatives of both kinds may be used as fluorescent markers in conjugation procedures. Hydrophilic dyes such as 6 and 6D are soluble in water or aqueous buffers and suitable for microinjections into the cells. Their conjugates with antibodies (e.g. obtained from the hydrophilic NHS esters 9 and 9D) produce low background in immunostaining experiments due to the 3.0 low affinity of the dye to intracellular components. The fluorescent dyes 6D and 9D containing 16-18 deuterium atoms in $CH_3$, $CH_2$ and CH groups nearby the xanthene core (see structures ID and IID above) and related compounds are characterized by a narrow and symmetrical molecular mass distribution pattern. They may be used as new molecular mass distribution tags for identification and quantification of the various substance classes (e.g. amines and thiols) in complex mixtures by means of mass-spectroscopy or HPLC MS. The ground state of the hydrophilic compound 6 may be depleted to an extent of 97±3% with powerful 633 nm laser pulses (ca. 12 kW/cm$^2$). Recovery time from the dark to the ground state was found to be 51.8±4.9 ms. If necessary, the recovery time may be shortened by using the pulse irradiation with UV light (375 nm). The ground state depletion parameters of the dye 6 are advantageous for its efficient use in the super resolution imaging techniques based on the switching between "bright" and "dark" states of an organic fluorophore.

The invention claimed is:

1. A compound having the general formula II:

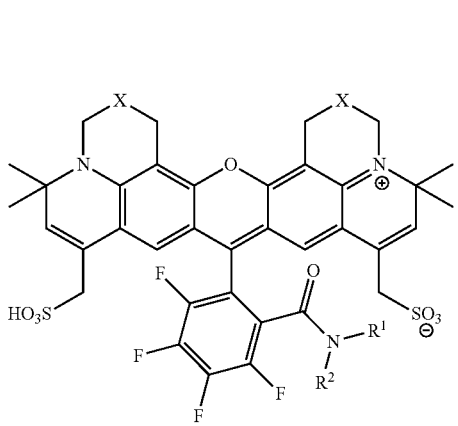

wherein $R^1$=an unsubstituted or substituted alkyl group, including a cycloalkyl group, or heterocycloalkyl group;

$R^2$=H, an unsubstituted or substituted (cyclo)alkyl group or heterocycloalkyl group, an unsubstituted or substituted aryl group or heteroaryl group, or any combination of such groups;

X=CH$_2$, C=O, C=NOR$^a$, C=NNR$^a$NR$^b$, CH(OR$^a$), O, S, SO or SO$_2$, with R$^a$ and R$^b$ independently being H or an organic residue.

2. The compound having the general formula II of claim 1, wherein $R^1$ is —[CH$_2$]$_n$—COOR$^3$ with $R^3$ being H or an organic residue, or $R^1$ is a —[CH$_2$]$_n$—R$^4$ group with R$^4$ being an N-linked maleimido group or a —S—S—R$^5$ group with R$^5$ being an organic residue, n is an integer from 1 to 21, and $R^2$ is H or an unsubstituted or substituted (cyclo)alkyl group or heterocycloalkyl group, or any combination of such groups, including $R^2$ being —[CH$_2$]$_n$—COOR$^3$ or —[CH$_2$]$_n$—R$^4$ as defined above for $R^1$.

3. The compound according to claim 2, having one of the following formulae

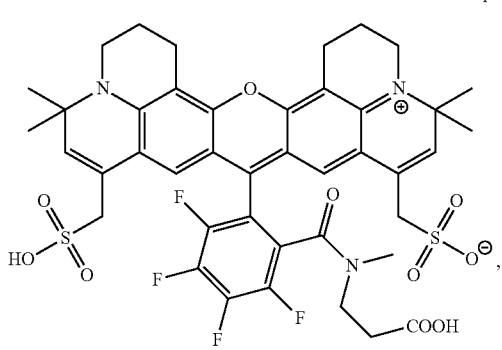

Compound 6

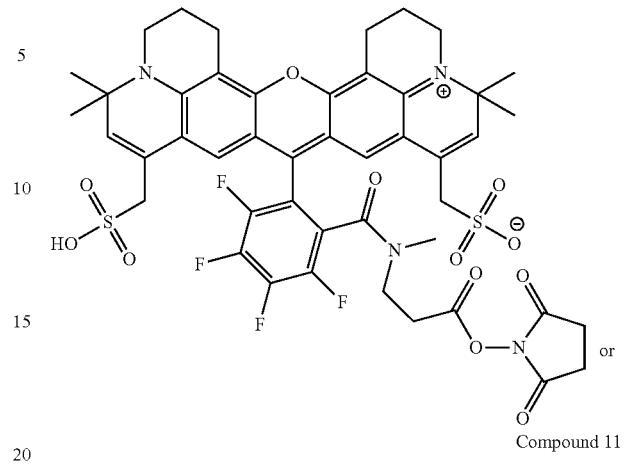

Compound 9 or

Compound 11

4. A compound having the general formula IID:

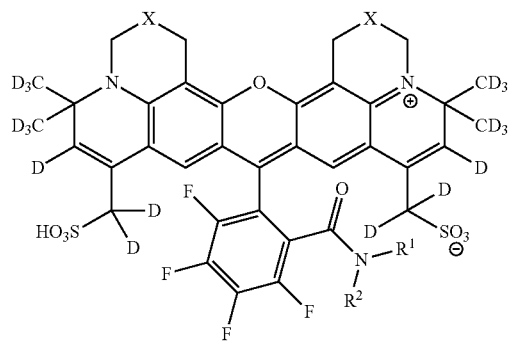

wherein
$R^1$=an unsubstituted or substituted (cyclo)alkyl group or heterocycloalkyl group;
$R^2$=H, an unsubstituted or substituted (cyclo)alkyl group or heterocycloalkyl group, an unsubstituted or substituted aryl group or heteroaryl group, or any combination of such groups;
X=CH$_2$, C=O, C=NOR$^a$, C=NNR$^a$NR$^b$, CH(OR$^a$), O, S, SO or SO$_2$, with R$^a$ and R$^b$ independently being H or an organic residue;
having 16-18 randomly distributed deuterium atoms in all positions denoted CD or CD$_3$.

5. The compound having the general formula IID of claim 4, wherein $R^1$ is —[CH$_2$]$_n$—COOR$^3$ with $R^3$ being H or an organic residue, or $R^1$ is a —[$CH_2$]$_n$—$R^4$ group with $R^4$ being an N-linked maleimido group or a —S—S—$R^5$ group with $R^5$ being an organic residue, n is an integer from 1 to 21, and $R^2$ is H or an unsubstituted or substituted (cyclo)alkyl group or heterocycloalkyl group, including $R^2$ being —[$CH_2$]$_n$—COO$R^3$ or —[$CH_2$]$_n$—$R^4$ as defined above for $R^1$.

6. The compound according to claim 5, having one of the following formulae:

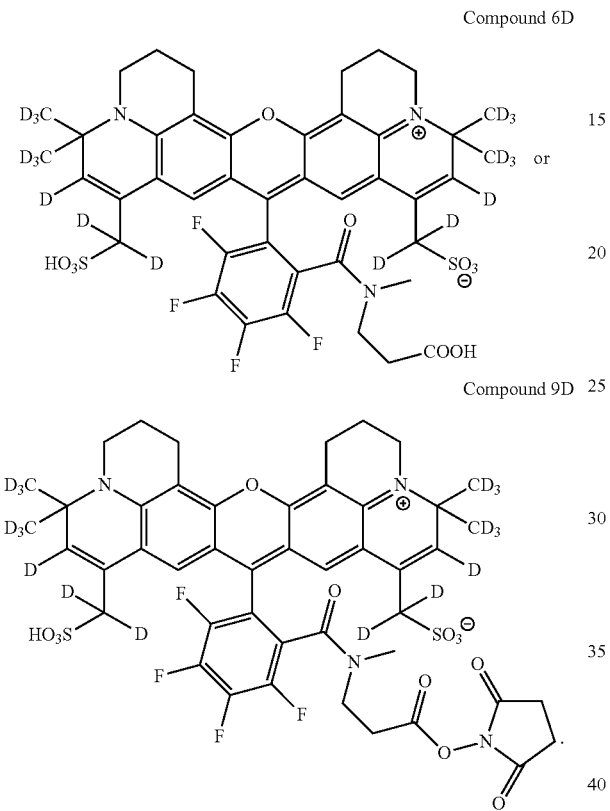

Compound 6D

Compound 9D

7. A fluorescent conjugate comprising the compound having the general formula II of claim 1 conjugated with a peptide, a protein, a lipid, a carbohydrate, a nucleic acid, or a toxin.

8. A method of performing spectroscopy or microscopy, said method comprising: providing the fluorescent conjugate according to claim 7, combining the fluorescent conjugate with a sample to be analyzed, and conducting a spectroscopic or microscopic analysis of the sample containing the fluorescent dye, wherein the spectroscopy or microscopy is optionally reversible saturable optically linear fluorescent transitions microscopy, stimulated emission depletion microscopy, fluorescence correlation spectroscopy, ground state depletion method, or conventional microscopy.

9. An immunostaining method comprising staining a sample to be analyzed with the compound according to claim 1 having the general formula II, wherein the compound is hydrophilic and provided in free form or attached to antibodies or other biomolecules.

10. A method for performing a mass spectrometry based analysis, said method comprising:
providing as a molecular mass distribution tag the compound according to claim 4 having the general formulae IID with 16-18 randomly distributed deuterium atoms in all positions denoted CD, CD2 or CD3, and having a narrow and symmetrical molecular mass distribution, and
performing the mass spectrometry based analysis, wherein the mass spectrometry based analysis is mass spectrometry, two-dimensional mass spectrometry (MS-MS) or any combination of mass spectrometry with chromatography or any other separation technique.

11. The compound having the general formula II of claim 1, having more than 2 atoms of H, C or N replaced by their stable isotopes ($^2$H, $^{13}$C and $^{15}$N).

12. The compound according to claim 11, having the following general formula IID:

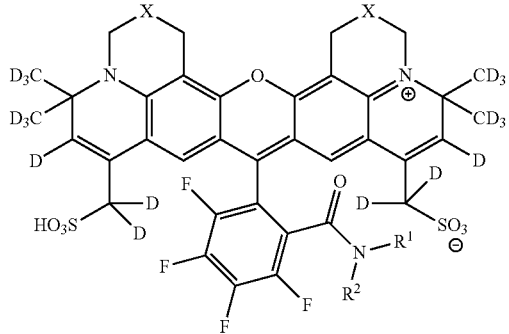

wherein
$R^1$=an unsubstituted or substituted (cyclo)alkyl group or heterocycloalkyl group;
$R^2$=H, an unsubstituted or substituted (cyclo)aryl group or heterocycloalkyl group, an unsubstituted or substituted aryl group or heteroaryl group, or any combination of such groups;
X=$CH_2$, C=O, C=NOR$^a$, C=NNR$^a$NR$^b$, CH(OR$^a$), O, S, SO, or $SO_2$, with $R^a$ and $R^b$ independently being H or and organic residue;
having 16-18 randomly distributed deuterium atoms in all positions denoted CD or CD$_3$.

13. The compound having the general formula II of claim 11, wherein $R^1$ is —[$CH_2$]$_n$—COY with Y being F, Cl or Br, and n being an integer from 1 to 21, or —[$CH_2$]$_n$—COO$R^3$ with $R^3$ being H or an organic residue, n being an integer from 1 to 21, and $R^2$ is H or an unsubstituted or substituted (cyclo)alkyl group or heterocycloalkyl group, including $R^2$ being —[$CH_2$]$_n$—COY or —[$CH_2$]$_n$—COO$R^3$ as defined above for $R^1$.

* * * * *